(12) United States Patent
Poetter et al.

(10) Patent No.: US 8,666,669 B2
(45) Date of Patent: Mar. 4, 2014

(54) METHOD FOR DETERMINING THE LIKELIHOOD THAT A TEST POLYNUCLEOTIDE SEQUENCE DIFFERS FROM A DRIVER POLYNUCLEOTIDE

(75) Inventors: Karl Poetter, Northcote (AU); Simon Foote, Fairfield (AU)

(73) Assignee: Genera Biosystems Limited (AU)

( * ) Notice: Subject to any disclaimer, the term of this patent is extended or adjusted under 35 U.S.C. 154(b) by 1766 days.

(21) Appl. No.: 10/296,860

(22) PCT Filed: May 29, 2001

(86) PCT No.: PCT/AU01/00635
§ 371 (c)(1),
(2), (4) Date: May 19, 2003

(87) PCT Pub. No.: WO01/92564
PCT Pub. Date: Dec. 6, 2001

(65) Prior Publication Data
US 2004/0014065 A1    Jan. 22, 2004

(30) Foreign Application Priority Data

May 29, 2000    (AU) ...................................... PQ7811

(51) Int. Cl.
*G01N 33/50* (2006.01)
(52) U.S. Cl.
USPC .......................................................... 702/19
(58) Field of Classification Search
None
See application file for complete search history.

(56) References Cited

U.S. PATENT DOCUMENTS

| | | |
|---|---|---|
| 5,582,970 A | 12/1996 | Wallace |
| 5,736,330 A | 4/1998 | Fulton |
| 5,981,180 A | 11/1999 | Chandler et al. |
| 6,051,374 A * | 4/2000 | Simons et al. .................. 435/5 |
| 6,057,107 A | 5/2000 | Fulton |
| 6,551,784 B2 * | 4/2003 | Fodor et al. .................. 435/6 |
| 2003/0039964 A1 * | 2/2003 | Giffard et al. .................. 435/6 |

FOREIGN PATENT DOCUMENTS

| | | |
|---|---|---|
| EP | 664339 | 7/1995 |
| EP | 852263 | 7/1998 |
| EP | 933431 | 8/1999 |
| WO | WO 97/38132 | 10/1997 |
| WO | WO 98/48048 | 10/1998 |

OTHER PUBLICATIONS

Cai et al., Flow cytometry-based DNA hybridization and polymorphism analysis, 1998, Proceedings of SPIE—the international society for optical engineering, vol. 3256, pp. 171-177.*
Ravaggi et al., Comparison of competitve and non-competitive reverse transcription-polymerase chain reaction (RT-PCR) for the quantification of hepatitis C virus (HCV) RNA, Journal of Virological Methods 65 (1997) pp. 123-129.*
Biotechniques 1994 vol. 17(3):566-573. Iitia, A. et al. "Detection of a point mutation using short oligonucleotide probes in allele-specific hybridization".
Biochem. Soc. Trans. 1995 vol. 23(1): 129S. Carpenter, K. et al. "The sensitivity of competitive hybridization for the detection of mutant p53 alleles in a background of wild type."
Anal. Biochem. 1997 vol. 251:270-279. Healey, B.G., et al. "Fibreoptic DNA sensor array capable of detecting point mutations."
Anal. Biochem. vol. 205(2): 193-199. Terouanne, B.,et al. "Quantitative and qualitative analysis of amplified DNA sequences by a competitive hybridization assay.", 1992.

* cited by examiner

*Primary Examiner* — Jason Sims
(74) *Attorney, Agent, or Firm* — Katten Muchin Rosenman LLP

(57) ABSTRACT

The present invention relates generally is a method for determining the likelihood that a test polynucleotide sequence differs from a driver polynucleotide sequence. More particularly, the present method uses fluorescence-based technology in the assessment of the results of competitive hybridization between polynucleotide sequences. The present method does not require nucleotide sequencing or gel electrophoresis and is capable of being multiplexed and automated. The methods of the present invention will find broad application in the analysis of polynucleotides, inter alia in genetic analysis, specific locus testing, genotyping, mutation detection, the discovery and detection of single nucleotide polymorphisms (SNPs) and mapping.

10 Claims, 16 Drawing Sheets

FIGURE 1

Test Sequences

```
              1          11         21         31
DRIVERN*   aAAGGGCCAAT CTGCTCACAC AGGATAGAGA GGGCAGGAGC
M-79A         f---A----- ---------- ---------- ----------
M-67A         f---------- --------A-- ---------- ----------
M-57G         f---------- ---------- -------G-- ----------
M-49T         f---------- ---------- ---------- ---T------
M-37T         f---------- ---------- ---------- ----------
M-23C         f---------- ---------- ---------- ----------
M-17G         f---------- ---------- ---------- ----------

41         51         61         71
MDRIVERN*  CAGGGCAGAG CATATAAGGT GAGGTAGGAT CAGTT      (SEQ ID NO:1)
M-79A      ---------- ---------- ---------- -----      (SEQ ID NO:2)
M-67A      ---------- ---------- ---------- -----      (SEQ ID NO:3)
M-57G      ---------- ---------- ---------- -----      (SEQ ID NO:4)
M-49T      ---------- ---------- ---------- -----      (SEQ ID NO:5)
M-37T      -----T---- ---------- ---------- -----      (SEQ ID NO:6)
M-23C      ---------- --------C- ---------- -----      (SEQ ID NO:7)
M-17G      ---------- ---------- -----G---- -----      (SEQ ID NO:8)
```

Target sequence**

```
MTARGETN   aAACTGATCCT ACCTCACCTT ATATGCTCTG CCCTGGCTCC
           TGCCCTCTCT ATCCTGTGTG AGCAGATTGG CCCTT    (SEQ ID NO:9)
```

Example of Homoduplex Preference Assay.

fig. 3. Gel image of gel based homoduplex preference assay.

Flow cytometric analysis of mutants and wild type controls in fast and slow conditions.

FIGURE 5

Mutation detection index calculation for ABI 377 test.

| DNA | NaCl (mM) | FAST | | | SLOW | | | MDI |
|---|---|---|---|---|---|---|---|---|
| | | FAM(F) | HEX(H) | H:F$^{(F)}$ | F | H | H:F$^{(S)}$ | H:F$^{(S)}$/ H:F$^{(F)}$ |
| 17G | 10 | 47181 | 1574 | 0.13 | 15 | 9193 | 2451 | 18370 |
| 17G | 20 | 62252 | 1932 | 0.12 | 15 | 13630 | 3634 | 29278 |
| 23C | 10 | 108987 | 6175 | 0.23 | 15 | 5947 | 1585 | 6997 |
| 23C | 20 | 50172 | 2385 | 0.19 | 15 | 21216 | 5657 | 29753 |
| 37T | 10 | 24435 | 1236 | 0.20 | 15 | 17517 | 4671 | 23086 |
| 37T | 20 | 72587 | 6736 | 0.37 | 15 | 19229 | 5127 | 13814 |
| 49T | 10 | 58155 | 6136 | 0.42 | 15 | 6567 | 1751 | 4149 |
| 49T | 20 | 30220 | 4141 | 0.55 | 15 | 19722 | 5259 | 9595 |
| 57G | 10 | 46044 | 4222 | 0.37 | 15 | 15085 | 4022 | 10967 |
| 57G | 20 | 61676 | 5613 | 0.36 | 15 | 19081 | 5088 | 13977 |
| 69A | 10 | 139162 | 8430 | 0.24 | 15 | 1631 | 434 | 1794 |
| 69A | 20 | 34104 | 1631 | 0.19 | 15 | 12435 | 3316 | 17334 |
| 79A | 10 | 36584 | 6391 | 0.70 | 15 | 14587 | 3889 | 5566 |
| 79A | 20 | 57098 | 7173 | 0.50 | 15 | 13570 | 3618 | 7201 |
| WT | 10 | 4123 | 2155 | 2.09 | 7590 | 3994 | 2 | 1 |
| WT | 20 | 7973 | 5145 | 2.58 | 8746 | 5061 | 2 | 0.9 |

SIFT SNP I

Inefficient: Arraying of PCR products is time consuming and difficult. This method does not allow for a standardized approach in which arrays can be manufactured ahead of time.

SIFT SNP II

SIFT SNP III
(Multi-SIFT SNP)

Sequence length polymorphism detection by SIFT

SEQUENCE LISTING

<160> NUMBER OF SEQ ID NOS: 12

<210> SEQ ID NO 1
<211> LENGTH: 75
<212> TYPE: DNA
<213> ORGANISM: human;DRIVER oligo

<400> SEQUENCE: 1
aagggccaat ctgctcacac aggatagaga gggcaggagc cagggcagag catataaggt     60
gaggtaggat cagtt                                                      75

<210> SEQ ID NO 2
<211> LENGTH: 75
<212> TYPE: DNA
<213> ORGANISM: human;M-79A oligo

<400> SEQUENCE: 2
aagagccaat ctgctcacac aggatagaga gggcaggagc cagggcagag catataaggt     60
gaggtaggat cagtt                                                      75

```
<210> SEQ ID NO 3
<211> LENGTH: 75
<212> TYPE: DNA
<213> ORGANISM: human;M-67A oligo

<400> SEQUENCE: 3
aagggccaat ctgctcaaac aggatagaga gggcaggagc cagggcagag catataaggt      60
gaggtaggat cagtt                                                      75

<210> SEQ ID NO 4
<211> LENGTH: 75
<212> TYPE: DNA
<213> ORGANISM: human;M-57G oligo

<400> SEQUENCE: 4
aagggccaat ctgctcacac aggatagaga gggcaggggc cagggcagag catataaggt      60
gaggtaggat cagtt                                                      75

<210> SEQ ID NO 5
<211> LENGTH: 75
<212> TYPE: DNA
<213> ORGANISM: human;M-49T oligo

<400> SEQUENCE: 5
aagggccaat ctgctcacac aggatagaga gggtaggagc cagggcagag catataaggt      60
gaggtaggat cagtt                                                      75

<210> SEQ ID NO 6
<211> LENGTH: 75
<212> TYPE: DNA
<213> ORGANISM: human;M-37T oligo

<400> SEQUENCE: 6
aagggccaat ctgctcacac aggatagaga gggcaggagc cagggtagag catataaggt      60
gaggtaggat cagtt                                                      75

<210> SEQ ID NO 7
<211> LENGTH: 75
<212> TYPE: DNA
<213> ORGANISM: human;M-23C oligo

<400> SEQUENCE: 7
aagggccaat ctgctcacac aggatagaga gggcaggagc cagggcagag catataaggc      60
gaggtaggat cagtt                                                      75

<210> SEQ ID NO 8
<211> LENGTH: 75
<212> TYPE: DNA
<213> ORGANISM: human;M-17G oligo

<400> SEQUENCE: 8
aagggccaat ctgctcacac aggatagaga gggcaggagc cagggcagag catataaggt      60
gaggtgggat cagtt                                                      75

<210> SEQ ID NO 9
<211> LENGTH: 75
<212> TYPE: DNA
<213> ORGANISM: human;MTARGETN
```

-continued

```
<400> SEQUENCE: 9
aactgatcct acctcacctt atatgctctg ccctggctcc tgccctctct atcctgtgtg        60
agcagattgg ccctt                                                        75

<210> SEQ ID NO 10
<211> LENGTH: 21
<212> TYPE: DNA
<213> ORGANISM: human;BL/6 specific forward primer

<400> SEQUENCE: 10
gctaaaaact gggactttgt g                                                 21

<210> SEQ ID NO 11
<211> LENGTH: 28
<212> TYPE: DNA
<213> ORGANISM: human;SJL specific forward primer

<400> SEQUENCE: 11
ggctcaagct aaaaactggg actttgtg                                          28

<210> SEQ ID NO 12
<211> LENGTH: 21
<212> TYPE: DNA
<213> ORGANISM: human;reverse primer

<400> SEQUENCE: 12
agtatccacc cccagagctt g                                                 21
```

METHOD FOR DETERMINING THE LIKELIHOOD THAT A TEST POLYNUCLEOTIDE SEQUENCE DIFFERS FROM A DRIVER POLYNUCLEOTIDE

FIELD OF THE INVENTION

The present invention relates generally is a method for determining the likelihood that a test polynucleotide sequence differs from a driver polynucleotide sequence. More particularly, the present method uses fluorescence-based technology in the assessment of the results of competitive hybridization between polynucleotide sequences. The present method does not require nucleotide sequencing or gel electrophoresis and is capable of being multiplexed and automated. The methods of the present invention will find broad application in the analysis of polynucleotides, inter alia in genetic analysis. specific locus testing, genotyping, mutation detection, the discovery and detection of single nucleotide polymorphisms (SNPs) and mapping.

BACKGROUND OF THE INVENTION

Bibliographic details of the publications referred to by the author in this specification are collected at the end of the description.

Reference to any prior art, in this specification is not, and should not be taken as an acknowledgment or any form of suggestion that this prior art is common general knowledge or forms part of the common general knowledge in Australia or any other country.

Molecular biology and genomic research is rapidly changing the scope as well as the focus of genetic research into causes of inherited diseases. With the rapid increase in primary DNA sequence information, the direct comparison of test DNA to known sequence as a way to characterise mutations is a methodology in need of development.

One approach to this problem is to sequence the unknown target DNA. DNA sequencing technology has become more commonplace and less cumbersome in recent years, but this approach is not suitable for high throughput mutation detection scanning due to low speed and high cost.

A second approach has exploited sequence specific conformational differences in either native (Orita, et al., 1989) or denaturing gradient (Foode. R, 1994) polyacrylamide gel electrophoresis (PAGE). These methods, in general, are relatively easy to perform, but are slow, and have a high rate of false negatives.

An elegant, but insensitive, approach to DNA mutation detection targets not DNA, but rather the DNA's expressed product. Functional assays of p53 (Schwartz, H. et al., 1998) proteins have been developed in which in vivo testing of cloned DNA in yeast can efficiently identify those chimeras carrying mutated gene fragments, as long as the product is nonfunctional. A similar in vitro approach, the protein truncation test (Roest, P. A. et al., 1993) has been developed for several cancer genes. This test, as the name implies, uses mRNA as a substrate in a transcription/translation experiment in which the synthesized protein product is sized by PAGE. The presence of a peptide shorter than a wild type control is evidence of a mutation resulting from either a deletion or a stop codon. These methods are quite useful for characterization of this type of major DNA aberration, but single base missense mutations are seldom detectable.

The fourth major category of mutation detection methodology depends on nucleic acid hybridization between known and unknown paralogs. If two or more different nucleic acid species are present in this reaction, heteroduplexes can form in which one or more mismatched base pairs exist. These mismatches can then be detected by enzymatic (Youil, R. et al., 1995; Parsons, B. L., 1997; Lu, A. L., 1992; Myers, R. M. et al., 1985) or chemical (Cotton R. G. et al., 1988) methods. While some of these methods are potentially quite useful for high-throughput screening because the detection of mismatches can be performed without gel electrophoresis (Parsons, B. L., 1997; Lu, A. L., 1992), the methods are not easily multiplexed. This approach, while simple in theory, has also spawned several new technologies for the detection of base mutations including DNA chips (Sosnowski, R. G. et al., 1997; Hacia, J. G. et al., 1996), mismatched duplexes found by denaturing high performance liquid chromatography (O'Donovan M. C. et al., 1998), and in-tube kinetic assays (Holland P. M. et al., 1991; Ririe, K. M. et al., 1997).

In the work leading up to the present invention, the inventors developed a DNA mutation detection system which applies competitive hybridization and differential labelling to produce a method capable of discriminating between single base mismatches in oligonucleotides. The method of the present invention is also capable of being multiplexed and automated.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

One aspect of the present invention provides a method for determining the likelihood that a test polynucleotide sequence differs from a driver polynucleotide sequence said method comprising preparing a composition comprising said test and driver polynucleotide sequences and a target polynucleotide sequence wherein under competitive hybridization conditions the driver polynucleotide sequence will more preferentially hybridize to the target polynucleotide sequence compared to said test polynucleotide sequence when said test polynucleotide sequence differs from said driver polynucleotide sequence by at least one nucleotide and wherein at least one of said test or driver polynucleotide sequence is labelled with a reporter molecule capable of providing an identifiable signal, subjecting said composition to competitive hybridization conditions and screening for the presence of a signal wherein the level of signal relative to a control is indicative of which polynucleotide sequence has competitively hybridized to said target sequence wherein an elevated level of driver polynucleotide hybridization to said target sequence is indicative that said test polynucleotide sequence differs from said driver polynucleotide sequence.

In a preferred but non-limiting embodiment, a driver and a target polynucleotide strand are substantially complementary.

Another aspect of the present invention provides a method for determining the likelihood that a test polynucleotide sequence differs from a driver polynucleotide sequence said method comprising preparing a composition comprising said test and driver polynucleotide sequences and a target polynucleotide sequence wherein under competitive hybridization conditions the driver polynucleotide sequence will more preferentially hybridize to the target polynucleotide sequence compared to said test polynucleotide sequence when said test polynucleotide sequence differs from said driver polynucleotide sequence by at least one nucleotide and wherein at least one of said test or driver polynucleotide sequences is labelled with a reporter molecule capable of providing an identifiable signal, subjecting said composition to competitive hybridization and non-competitive hybridization conditions and screening for the presence of a signal wherein the level of signal relative to a control is indicative of which polynucleotide sequence has competitively hybridized to said target sequence wherein an elevated level of driver polynucleotide hybridization to said target sequence is indicative that said test polynucleotide sequence differs from a said driver polynucleotide sequence.

Yet another aspect of the present invention provides a method for determining the likelihood that a test polynucleotide sequence differs from a driver polynucleotide sequence said method comprising preparing a composition comprising said test and driver polynucleotide sequences and a target polynucleotide sequence wherein under competitive hybridization conditions the driver polynucleotide sequence will more preferentially hybridize to the target polynucleotide sequence compared to said test polynucleotide sequence when said test polynucleotide sequence differs from said driver polynucleotide sequence by at least one nucleotide and wherein at least one of said test or driver polynucleotide sequence is labelled with a reporter molecule capable of providing an identifiable signal, subjecting said composition to competitive hybridization conditions and screening for the presence of a signal wherein the level of signal relative to a control is indicative of which polynucleotide sequence has competitively hybridized to said target sequence wherein an elevated ratio of driver polynucleotide hybridization to said target sequence is indicative that said test polynucleotide sequence differs from a said driver polynucleotide sequence, said ratio being determined by the following formula:

$$(D:T)_{comp}/(D:T)_{non\text{-}comp}$$

wherein
D is the driver-label;
T is the test-label;
Comp is the D:T ratio under competitive hybridization conditions; and
Non-comp is the D:T ratio under control conditions.

Still yet another aspect of the present invention provides a method for determining the likelihood that a test polynucleotide sequence differs from a driver polynucleotide sequence said method comprising preparing a composition comprising said test and driver polynucleotide sequences and a target polynucleotide sequence wherein under slow hybridization conditions the driver polynucleotide sequence will more preferentially hybridize to the target polynucleotide sequence compared to said test polynucleotide sequence when said test polynucleotide sequence differs from said driver polynucleotide sequence by at least one nucleotide and wherein at least one of said test or driver polynucleotide sequence is labelled with a reporter molecule capable of providing an identifiable signal, subjecting said composition to competitive hybridization and non-competitive hybridization conditions and screening for the presence of a signal wherein the level of signal relative to a control is indicative of which polynucleotide sequence has competitively hybridized to said target sequence wherein an elevated ratio of driver polynucleotide hybridization to said target sequence is indicative that said test polynucleotide sequence differs from a said driver polynucleotide sequence said ratio being determined by the following formula:

$$(D:T)_{comp}/(D:T)_{non\text{-}comp}$$

wherein
D is the driver-label;
T is the test-label;
Comp is the D:T ratio under competitive hybridization conditions; and
Non-comp is the D:T ratio under non-competitive hybridization conditions.

Even yet another aspect of the present invention provides a method for determining the likelihood that a test polynucleotide sequence differs from an driver polynucleotide sequence said method comprising preparing a composition comprising said test and driver polynucleotide sequences and a target polynucleotide sequence wherein the target polynucleotide is immobilized and wherein under competitive hybridization conditions the driver polynucleotide sequence will more preferentially hybridize to the target polynucleotide sequence compared to said test polynucleotide sequence when said test polynucleotide sequence differs from said driver polynucleotide sequence by at least one nucleotide and wherein at least one of said test or driver polynucleotide sequence is labelled with a reporter molecule capable of providing an identifiable signal, subjecting said composition to competitive hybridization conditions and screening for the presence of a signal wherein the level of signal relative to a control is indicative of which polynucleotide sequence has competitively hybridized to said target sequence wherein an elevated level of driver polynucleotide hybridization to said target sequence is indicative that said test polynucleotide sequence differs from a said driver polynucleotide sequence.

Even yet another aspect of the present invention provides a method for determining the likelihood that a test polynucleotide sequence differs from a driver polynucleotide sequence said method comprising preparing a composition comprising said test and driver polynucleotide sequences and a target polynucleotide sequence wherein the target polynucleotide is immobilized and wherein under competitive hybridization conditions the driver polynucleotide sequence will more preferentially hybridize to the target polynucleotide sequence compared to said test polynucleotide sequence when said test polynucleotide sequence differs from said driver polynucleotide sequence by at least one nucleotide and wherein at least one of said test or driver polynucleotide sequence is labelled with a reporter molecule capable of providing an identifiable signal, subjecting said composition to competitive hybridization conditions, subjecting the immobilized polynucleotide sequences to a washing step to remove unhybridized polynucleotide and screening for the presence of a signal wherein the level of signal relative to a control is indicative of which polynucleotide sequence has competitively hybridized to said target sequence wherein an elevated level of driver polynucleotide hybridization to said target sequence is indicative that said test polynucleotide sequence differs from a said driver polynucleotide sequence.

Still yet another aspect of the present invention provides a method for determining the likelihood that a test polynucleotide sequence differs from a driver polynucleotide sequence said method comprising preparing a composition comprising said test and driver polynucleotide sequences and a target polynucleotide sequence wherein the target polynucleotide is immobilized and wherein under competitive hybridization conditions the driver polynucleotide sequence will more preferentially hybridize to the target polynucleotide sequence compared to said test polynucleotide sequence when said test polynucleotide sequence differs from said driver polynucleotide sequence by at least one nucleotide and wherein at least one of said test or driver polynucleotide sequence is labelled with a fluorescent reporter molecule, subjecting said composition to competitive hybridization conditions and screening for the presence of a signal by flow cytometry and/or other equivalent procedure wherein the level of signal relative to a control is indicative of which polynucleotide sequence has competitively hybridized to said target sequence wherein an elevated level of driver polynucleotide hybridization to said target sequence is indicative that said test polynucleotide sequence differs from a said driver polynucleotide sequence.

BRIEF DESCRIPTION OF THE FIGURES

FIG. 1 illustrates the oligonucleotide sequences used in the homoduplex preference assay. The sequences correspond to base 82 to 8 nucleotide upstream of the transcription start site of the human B-globin gene (Casey, J., 1977). Wild type and 7 allelic sequences differing by one bases pair are shown as well as the exact complement (MTARGETN) to the wild type sequence. In the figure a=amine terminated (5') end used for the post synthesis addition of either FAM, HEX, or biotin tags via NHS ester conjugation. For MTARGETN, amine end was used for conjugation to carboxylated beads. f=FAM label (during synthesis).

\* MDRIVERN sequence is the wild type standard. The HEX labelled MDRIVEN is referred to as the driver in the description.

\*\* The FAM labelled sequences differ from MDRIVEN by single point mutations. These sequences are referred to as test sequences in following discussions.

\*\*\* MTARGETN sequence is complement of MDRIVENRN and is referred to as target in description of the experimental method.

Figure 2A:
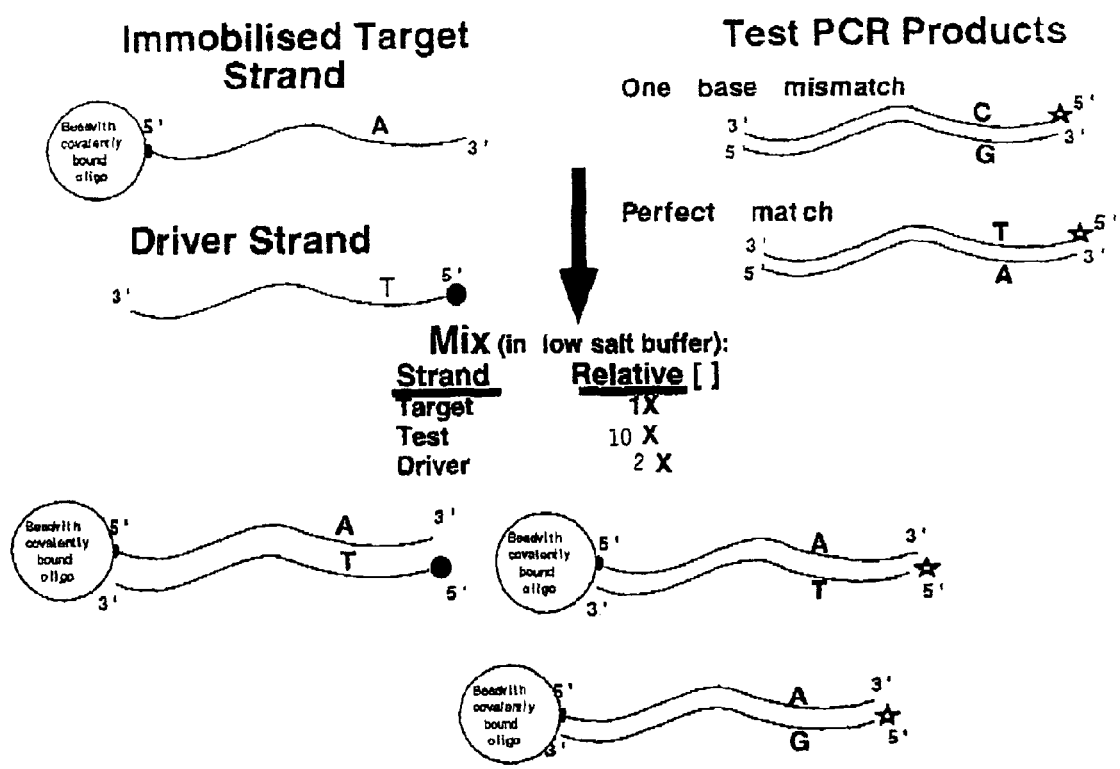

FIG. 2a is a diagrammatic representation of the Sequence Identification by Flow Test (SIFT) assay.

Figure 2B:
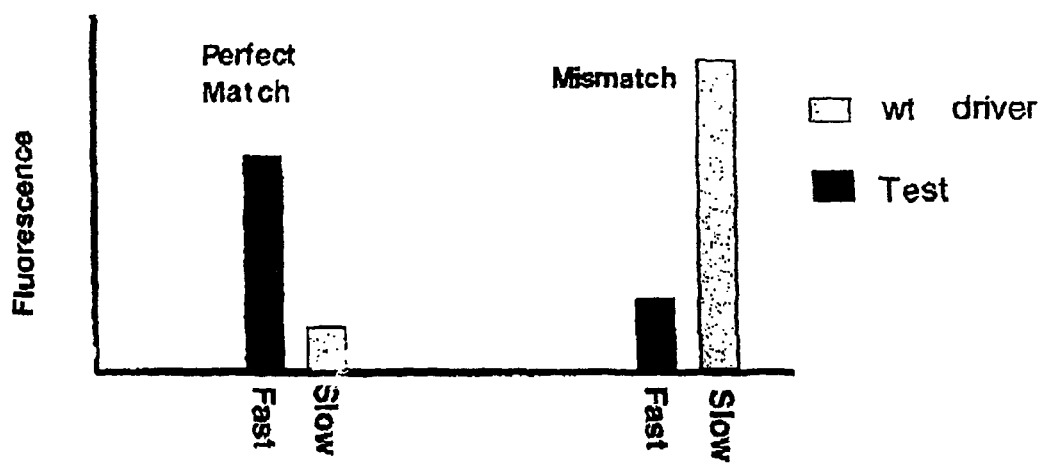

FIG. 2b is a graphical representation of the mean fluorescence (associated with wild type driver or test polynucleotides) detected on the target strand under fast (non-competitive) and slow (competitive) hybridization conditions in the homoduplex preference assay.

Figure 3:
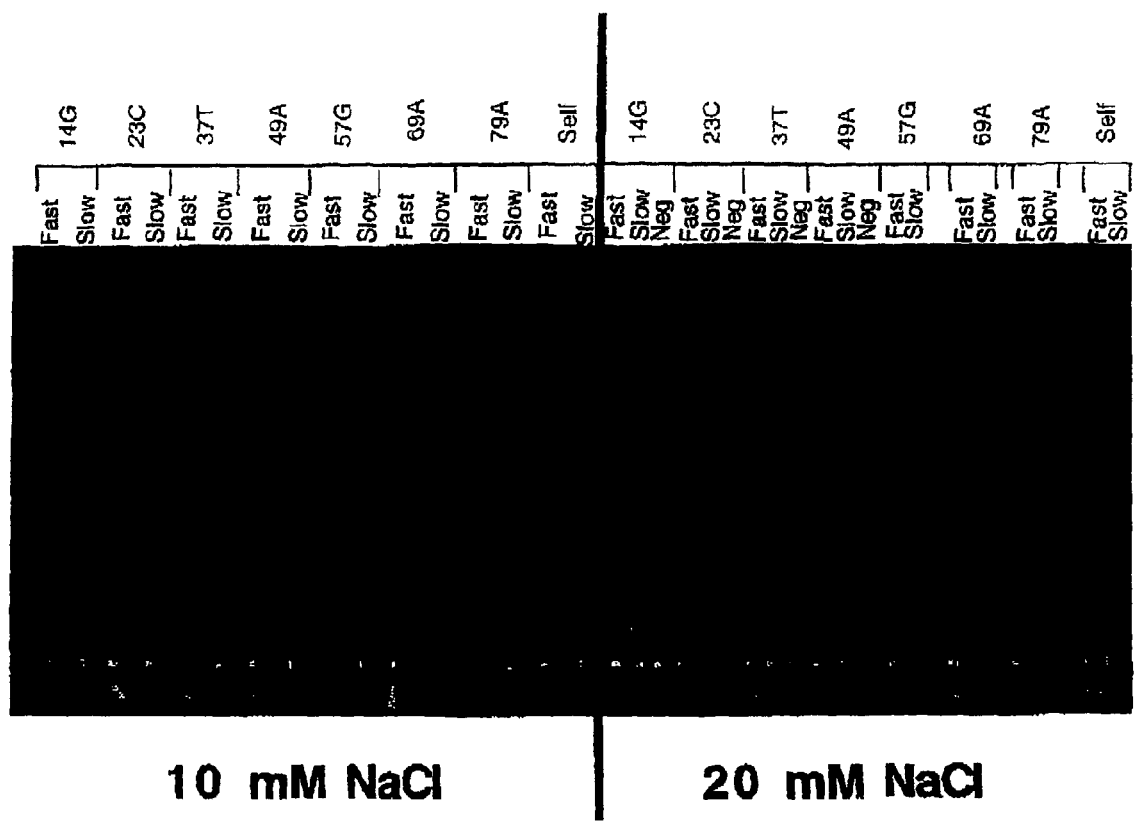

FIG. 3 is a photographic representation of labelled polynucleotides after PAGE.

Figure 4:
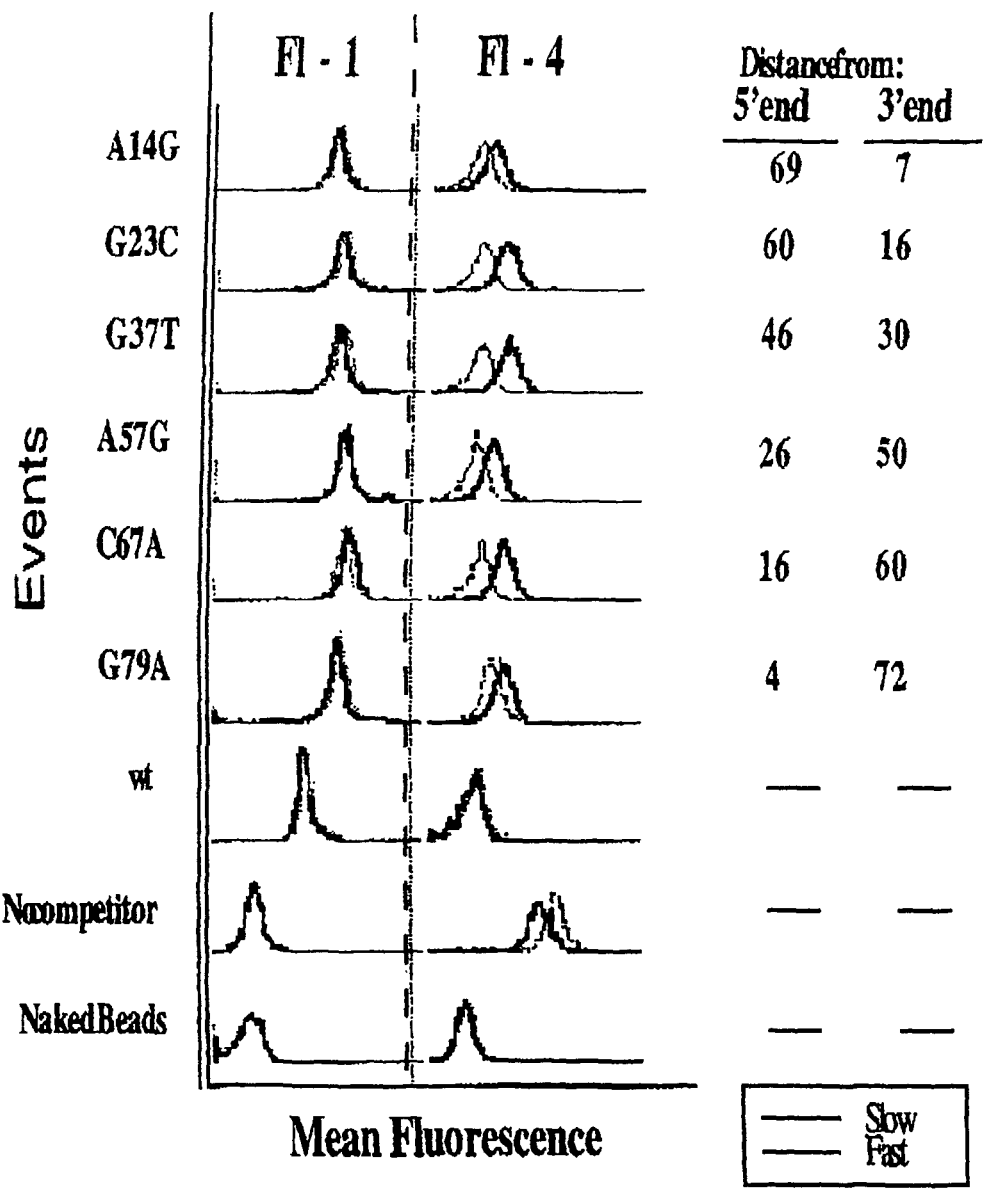

FIG. 4 illustrates the results of flow cytometry experiments where difference-bearing polynucleotides (A14G, G23C, G37T, A57G, C67A, G79A) show positive shifts in driver fluorsecence (FL-1) under competitive hybridization conditions.

FIG. 5 tabulates the ratios of driver to test label in gel based homoduplex preference assays in which the test DNA is labelled with FAM and the wild type DNA is labelled with HEX. Hybridization was performed under fast (non-competitive) and slow (competitive) conditions.

Figure 6:
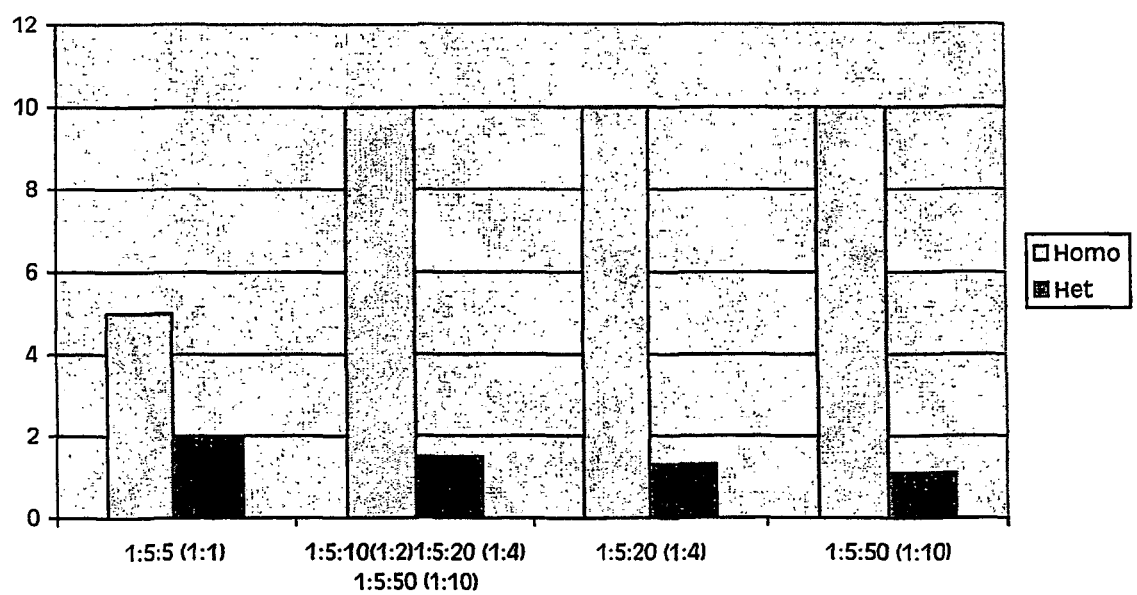

FIG. 6 is a graphical representation showing the relative competitive advantage of homoduplex over mutant, when differing ratios of target: wild type (driver) competitor:test are used. Ratios are given in terms of Target:wild type competitor:test. Ratios in parentheses are ratios of wild type:test only. Numbers on left axis represent relative competitive advantage of homoduplex over mutant.

Figure 7:
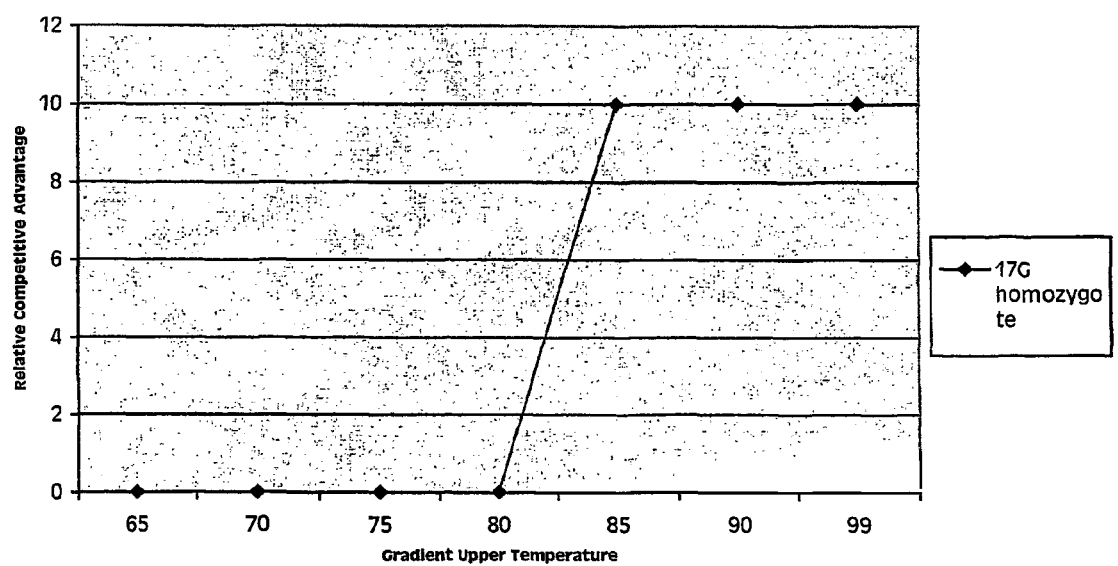

FIG. 7 is a graphical representation showing the upper temperature limit. Components are 75-mer Target and Spacer Hex labeled competitor. The test strand is a fluoresceinated mutant 17G polynucleotide. Numbers on the bottom axis represent temperature at which gradient started. All gradients were 10 minutes per degree drop and went from upper temperature to 50° C. Numbers on left axis represent relative competitive advantage.

Figure 8:
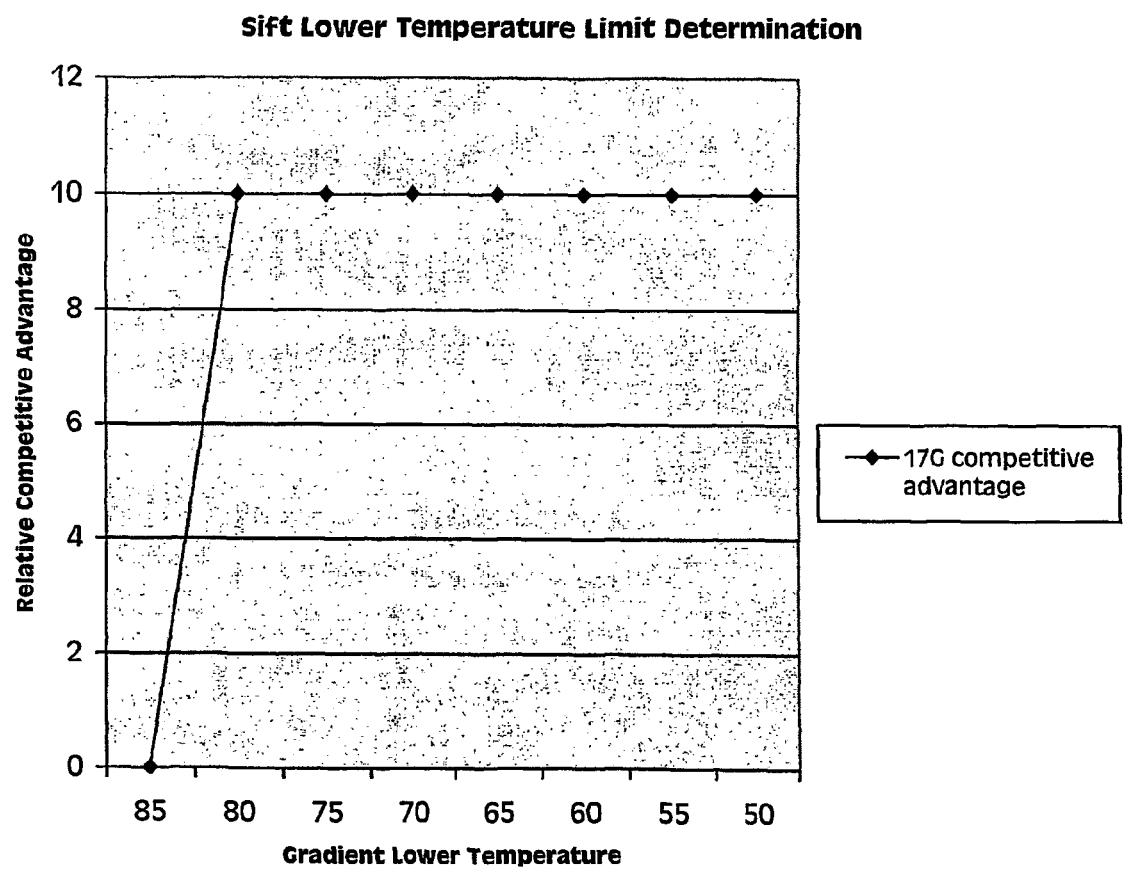

FIG. 8 is a graphical representation showing the result of experiments to define a lower temperature limit. Components are 75-mer Target and Spacer Hex labeled competitor. Test strand is fluoresceinated mutant 17G. Numbers on bottom axis represent temperature at which gradient started. All gradients were 10 minutes per degree drop and went from upper temperature to 50° C. Numbers on left axis represent relative competitive advantage.

Figure 9:
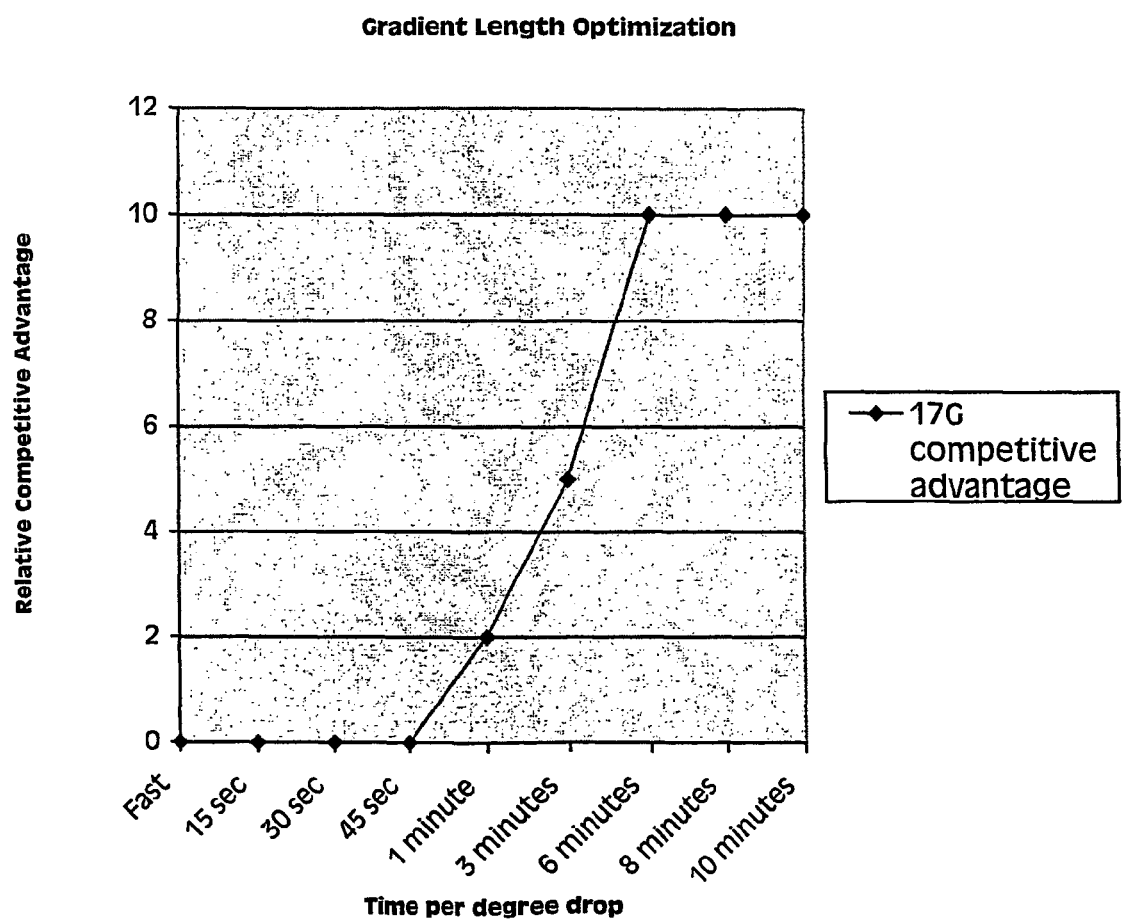

FIG. 9 is a graphical representation of the result of experiment to define optimum gradient lengths. Components are 75-mer Target and Spacer Hex labeled competitor. The numbers on the bottom axis represent the time for each degree drop. The numbers on the left axis represent the relative competitive advantage of homoduplex formation.

Figure 10:
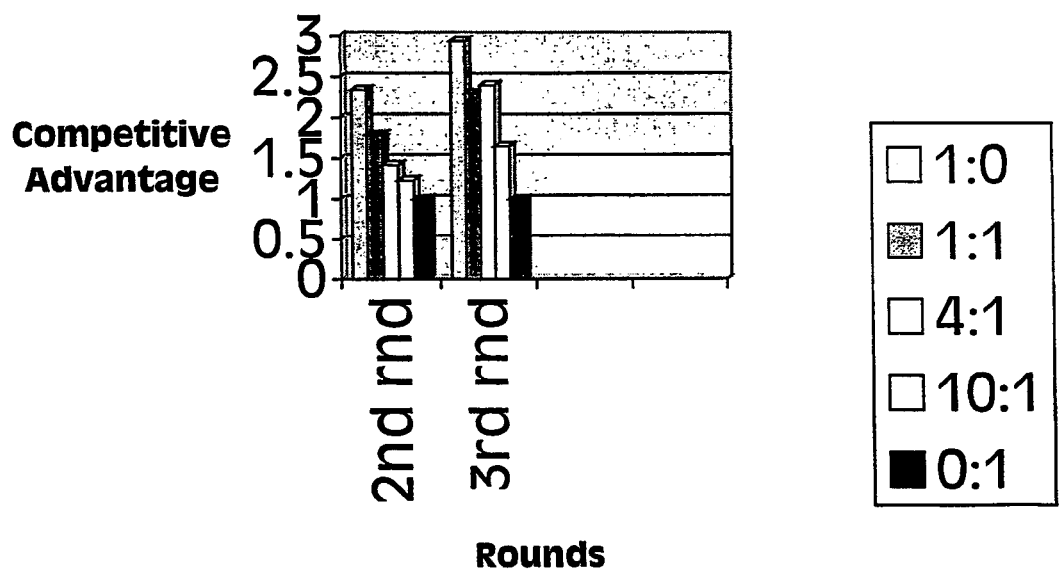
Figure 11:
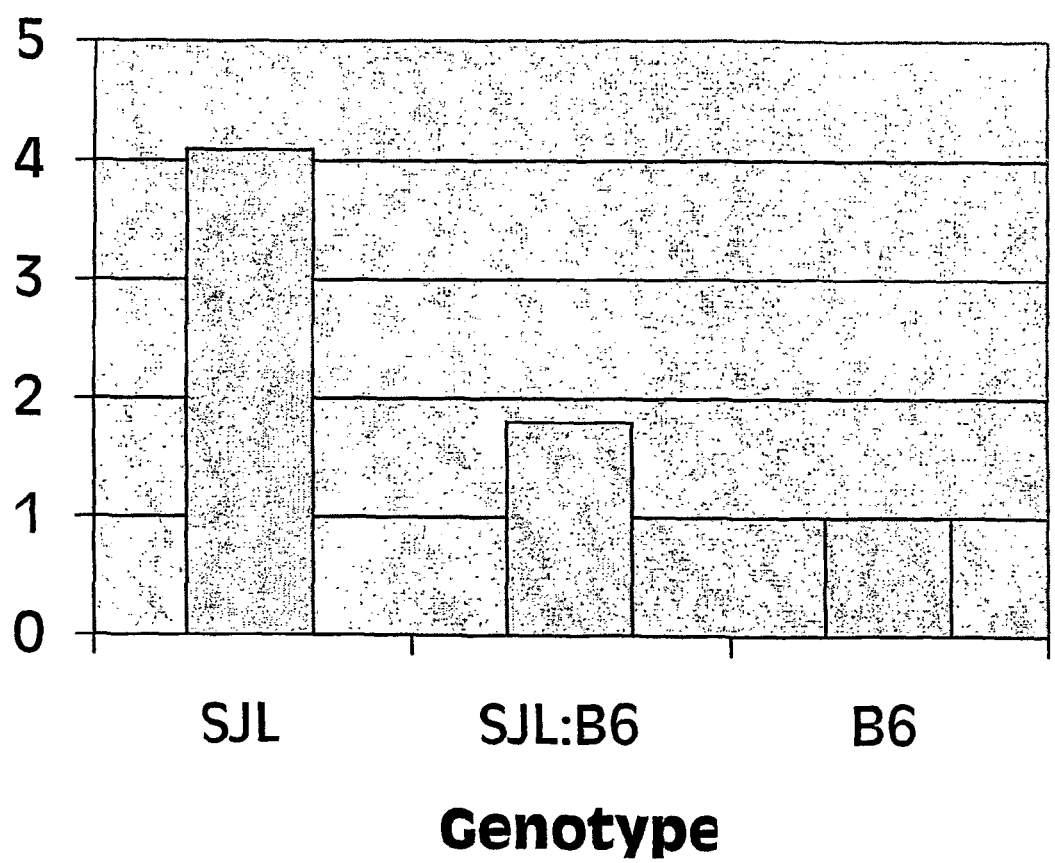

FIG. 10 is a graphical representation showing enrichment of polymorphic nucleotides after further rounds of SIFT. Mutant:wild type ratios of 0:1, 1:1, 4:1, 10:1 and 1:0 were subjected to SIFT and unbound supernatants enriched for mutant or polymorphic sequences by subjecting the supernatants to further rounds of SIFT. The MDI index was calculated as described herein FIG. 11 is a graphical representation of the results of a SIFT protocol showing differential annealing of PCR stands differing by a single base. Test DNAs for homozygous mutant (SLJ), heterozygote (SJL:B6) and wild type control were scored for fluorescence on AB1377. The MDI index was calculated as described herein.

Figure 12:
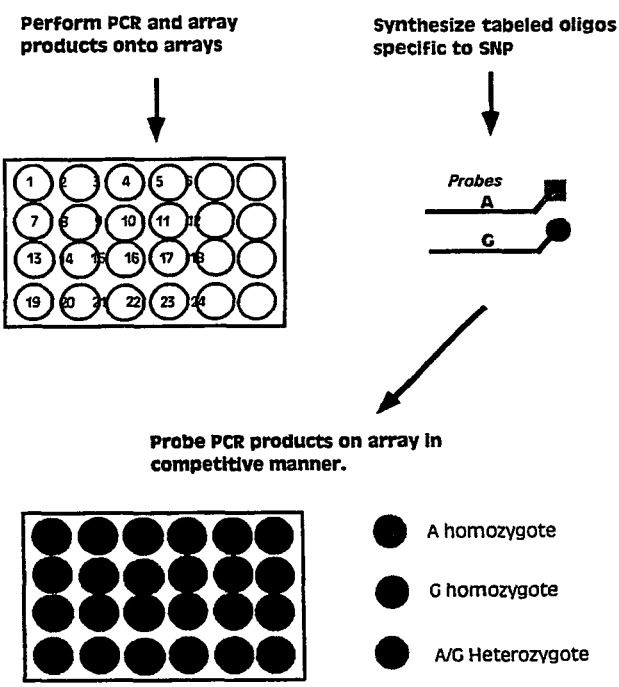
Figure 12:
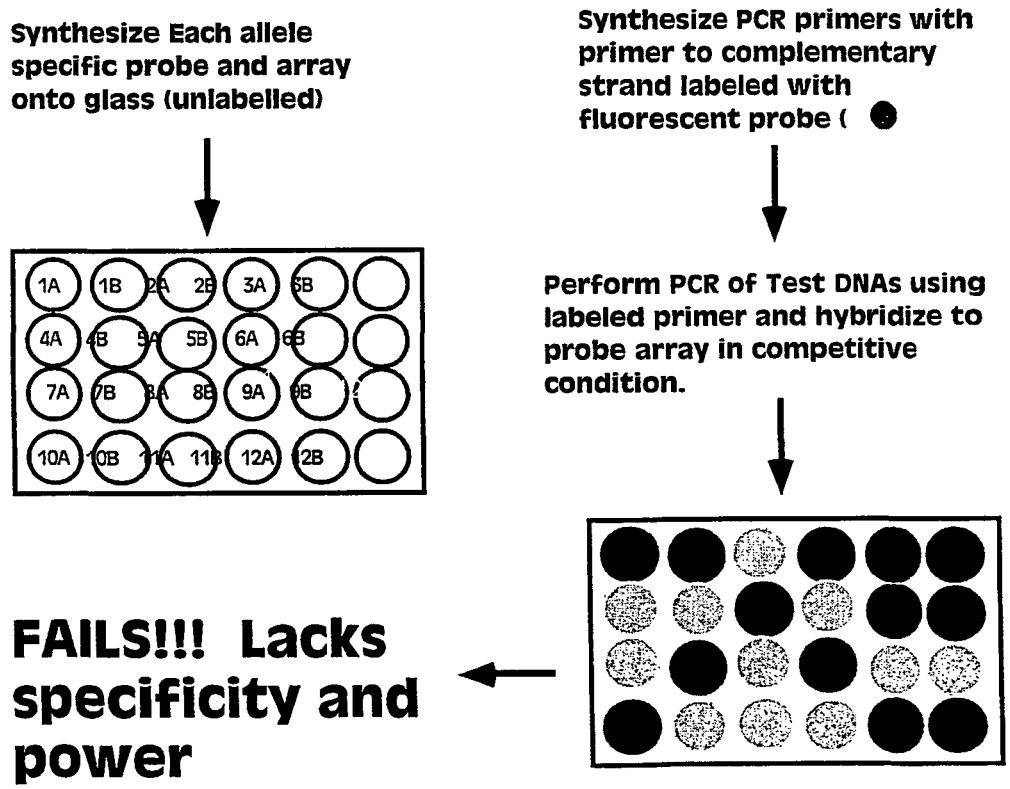
Figure 12:
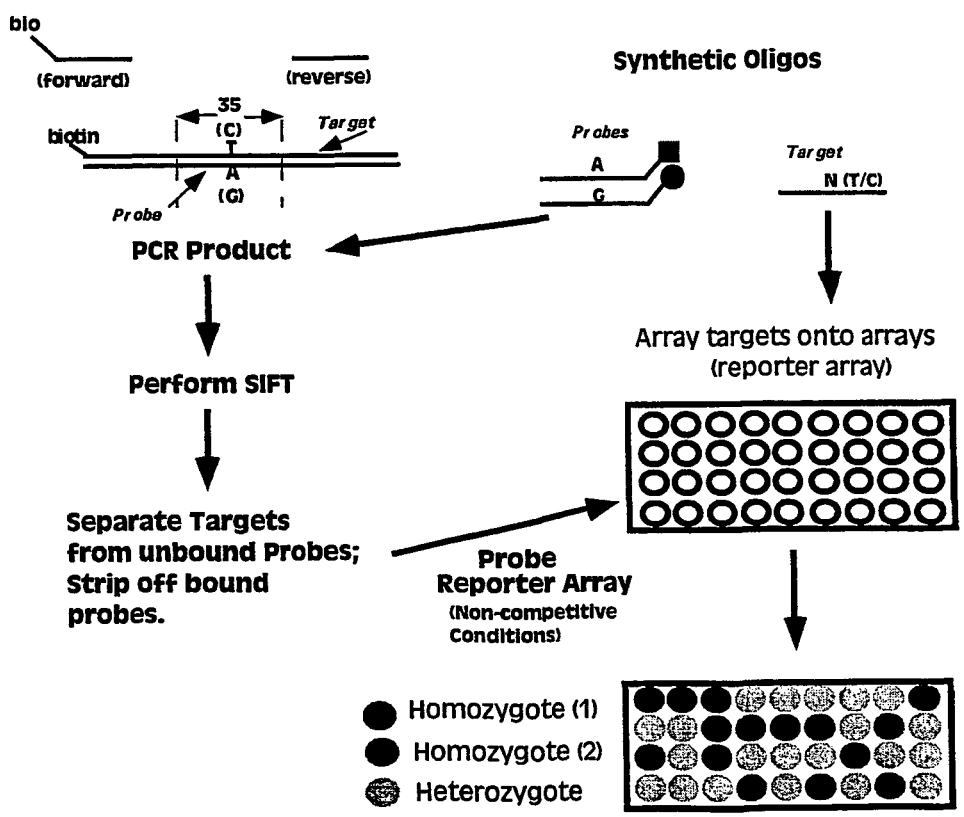

FIG. 12 is a graphical illustration of three proposed SIFT protocols adapted for SNP discovery and detection.

Figure 13:
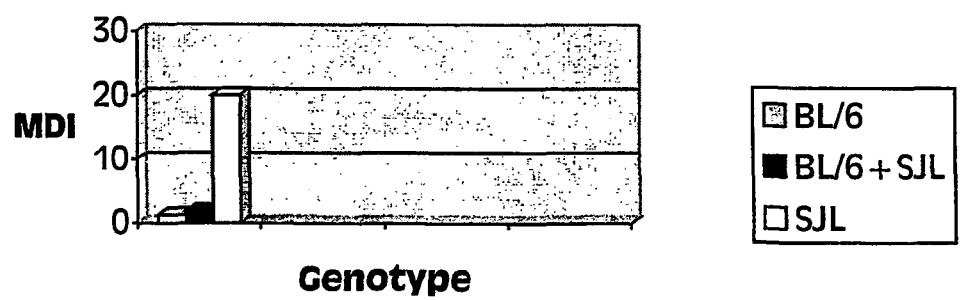

FIG. 13 is a graphical representation of results when SIFT is used to detect sequence length polymorphisms. BL/6 DNA from locus 835 was used as target with forward primer biotinylated and reverse primer labeled with TMR Test DNAs consisting of BL/6, SJL, or Heterozygote of equal amounts of BL/6 and SJL, were made by amplification with unlabeled forward primers and TMR labeled reverse primers. After competitive hybridization, DNA was bound to beads. Fluorescence was measured by GENESCAN.

DETAILED DESCRIPTION OF THE PREFERRED EMBODIMENTS

The present invention is predicated, in part, on the initial development of a method for determining the likelihood of a difference of at least one nucleotide between fluorescently labelled polynucleotides by measuring the fluorescence attached to an immobilized target polynucleotide to which the polynucleotides under comparison are allowed to hybridize under slow hybridization conditions. Under these hybridization conditions, the polynucleotide having a sequence most like the target polynucleotide sequence will preferentially hybridize to the target polynucltide. Accordingly, the fluorsecent label attached to the preferentially hybridizing polynucleotide will predominate over the fluorescent label attached to the polynucleotide which is less complementary to the target polynucleotide. The method provides a rapid means for analysing the results of competitive hybridization without need for any purification or washing steps. By assessing the results of hybridizations performed under both competitive and non-competitive conditions, a mutation detection index (MDI) ratio may be calculated to indicate whether a test polynuclotide sequence differs from a driver polynucleotide sequence. In fact, any ratio may be used provided it compares the input and output ratios of the different molecular species.

Accordingly, one aspect of the present invention provides a method for determining the likelihood that a test polynucleotide sequence differs from a driver polynucleotide sequence said method comprising preparing a composition comprising said test and driver polynucleotide sequences and a target polynucleotide sequence wherein under competitive hybridization conditions the driver polynucleotide sequence will more preferentially hybridize to the target polynucleotide sequence compared to said test polynucleotide sequence when said test polynucleotide sequence differs from said driver polynucleotide sequence by at least one nucleotide and wherein at least one of said test or driver polynucleotide sequence is labelled with a reporter molecule capable of providing an identifiable signal, subjecting said composition to competitive hybridization conditions and screening for the presence of a signal wherein the level of signal relative to a control is indicative of which polynucleotide sequence has competitively hybridized to said target sequence wherein an elevated level of driver polynucleotide hybridization to said target sequence is indicative that said test polynucleotide sequence differs from said driver polynucleotide sequence.

Reference herein to a polynucleotide includes reference to double or single stranded DNA, cDNA or genomic DNA, mRNA, cRNA, tRNA or a DNA/RNA hybrid. In one embodiment of the present invention, double stranded DNA is isolated from a biological sample and subjected directly to the present method. In another embodiment the polynucleotide is first subjected to amplification or amplification and labelling. Isolated mRNA is reverse transcribed to produce cDNA which is again either used directly in the present method or is first subjected to amplification or amplification and labelling. The biological sample is any sample putatively containing polynucleotides.

Reference to a difference between polynucleotide sequences includes broad reference to any modification to a polynucleotide sequence which is known in the art to confer altered hybridization qualities such as, for example, one or more base changes. In a preferred aspect, the difference is a mutation. The mutation may be, for example, a deletion, addition, substitution, inversion or duplication of one or more nucleotides in a polynucleotide. The mutation may in addition be a naturally occurring polymorphism. The polynucleotide may comprise naturally occurring bases of DNA or RNA or may comprise modified bases. The polynucleotide may also comprise naturally occurring sugar and backbone moeties or these may also be modified. Any other part of the polynucleotide may be modified by methods which are known by those skilled in the art.

During an amplification step nucleotide analogues may be incorporated which assist in the subsequent labelling or detection steps.

Reference to a polynucleotide sequence is not limited to sequences derived from any particular organism or species and includes sequences derived from a eukaryotic organism such as but not limited to a human, primate, livestock animal (e.g. sheep, cows, pigs, horses), laboratory test animals (e.g. mice, rats, rabbits), companion animals (e.g. dogs, cats), avian species, reptiles, fish, insects, arachnids, yeast and eukaryotic parasites such as *Plasmodium* species as well as plants. The eukaryotic organisms including plants may be naturally occurring, maintained in an artificial environment or be the product of genetic engineering or other genetic modification. In another embodiment, the biological sample is from a prokaryotic or eukaryotic micro-organism. In yet another embodiment, the biological sample is a virus or viral preparation including viral nucleic acid sequences alone or integrated into microbial or eukaryotic genome.

In one embodiment the method of the present invention is used to detect an infection or condition or disease condition or a propensity to develop an infection, condition or disease condition such as, for example, Achondroplasia, Adrenal Hypoplasia, Congenital Alagille Syndrome, α-1-Antitrypsin Deficiency, Aneuploidy Screen, Angelman Syndrome, UBE3A Sequence Analysis, APC Gene Mutation, Ashkenazic Genetic Disease Screen, Bloom Syndrome, BRCA1 and BRCA2, Canavan Disease, CFTR 5T Variant Analysis, CBAVD (Congenital Bilateral Absence Of Vas Deferens), Charcot-Marie-Tooth Disease Type 1A, Cystic Fibrosis, Dentatorubral Pallidoluysian Atrophy (DRPLA), Digeorge/Velocardiofacial Syndrome, Duchenne/Becker Muscular Dystrophy, Factor VIII Deficiency, Fragile X Syndrome, Friedreichs Ataxia, Gaucher Disease, Hemochromatosis, Hemophilia A, Hereditary Neuropathy With Liability To Pressure Palsies (HNPP), Heterozygosity, HLA(MHC), Huntington Disease, Hypertrophic cardiomyopathy, Hypoxanthine Phosphoribosyl Transferase, Incontinentia Pigmenti, Inherited Peripheral Neuropathies, Kennedy Disease, Spinobulbar Muscular Atrophy, Langer-Giedion Syndrome, Machado-Joseph Disease, Miller-Dieker Syndrome, Isolated Lissencephaly, MTHR Variant Analysis, Multiple Exostoses, Myotonic Dystrophy, Pelizaeus-Merzbacher Disease, Prader-Willi Syndrome, Prothrombin (Factor II), Rett Syndrome, RHD Molecular Typing, Rubinstein-Taybi Syndrome, Sickle Cell And Hemoglobin SC Disease, Smith-Lemli-Opitz Syndrome (SLO), Smith-Magenis Syndrome, Spinal Muscular Atrophy (SMA), Tay-Sachs Disease, Thrombophilia, Trichorhinophalangeal Syndrome, Velocardiofacial Syndrome, Williams Syndrome, X-linked Ichthyosis, Prelingual Nonsyndromic [Connexin 26 gene], Deafness, Mitochondrial Gene (A1555G), Neurofibromatosis (NF-1), Paraganglioma, Phenylketonuria, Werdnig-Hoffman Syndrome, Kugelberg-Welander Syndrome, Spinal and Bulbar Muscular Atrophy, Spinocerebellar Ataxia Type I, Spinocerebellar Ataxia Type II, Spinocerebellar Ataxia Type II, Spinocerebellar Ataxia Type VI, Spinocerebellar Ataxia Type VII, Spinocerebellar Ataxia Type VIII, Von Hippel-Lindau syndrome, Waardenburg syndrome (Type I), Wilson's disease, BCR/ABL Translocation(Philadelphia chromosome), Familial Mediterranean Fever, Familial polyposis coli, Multiple endocrine Neoplasia Type 1, Polycystic Kidney Disease (Adult), Prothrombin Gene Mutation (20210A), Uniparental Disomy [for specified chromosomes], X-linked lymphoproliferative disease, Y-Chromosome Specific DNA for Mosaicism [e.g., Turner's syndrome/Gonadal dysgenesis], Y-Chromosome Microdeletions for Azoospermic/Oligospermic males (e.g., DAZ deletion), Kallman syndrome, PML/RARA translocation,t(15; 17), Rapid FISH for [21, 18, 13, X and Y], Smith-Magenis Syndrome, Subtelomeric rearrangements, Translocations (Cryptic), ornithine transcarbamylase deficiency, resistance to activated protein C, Rh testing, fetal sex determination tyrosinemia type 1 (linkage analysis), zygosity Apolipoprotein E genotype, FMR-1 Triplet Repeat and Methylation, Lyme Disease, Cytomegalovirus (CMV), Hepatitis C virus (HCV), Hepatitis B virus (HBV), Human T-cell lymphoma/ leukemia virus-I (HTLV-I), Human T-cell lymphoma/leukemia virus-II (HTLV-II), Human immunodeficiency virus (HIV-I), Quantitative hepatitis C virus (HCV), Quantitative cytomegalovirus (CMV), Influenza virus, Parainfluenza virus, Adenoviruses (Types 2+5), HSV, VZV, HPV generic, HPV 6, 11, 16, 18, 31, 33, *Moraxella Catarrhalis, Streptococcus pneumonia, Haemophilus influena, Bordetella pertussis, Legionella* spp, Crigler-Najjar, Epidermolysis Bullosa Simplex, Hypokalemic periodic paralysis (HOKPP1) Leber's hereditary optic neuropathy (LHON), Marfan Syndrome MCAD 201450 A985G common mutation Sequence exons 7 and 11 for rare mutations MELAS A3243G mutation, MTTL1, MTTK, NARP/Leigh's encephalopathy, MEN2A, MEN2B, FMTC, Retinoblastoma, Stickler Syndrome.

Reference to "competitive hybridization" includes reference to hybridization conditions which permit one polynucleotide to hybridize preferentially to a complementary or partially complementary sequence compared to another sequence which is less complementary or which has other modifications which reduce its annealing capability.

Hybridization between complementary bases occurs under a wide variety of conditions and is generally dependent upon the temperature, salt concentration, electrostatic strength and buffer composition. For example, non-competitive or low stringency hybridization includes and encompasses from at least about 0 to at least about 15% v/v formamide and from at least about 1 M to at least about 2 M salt for hybridization, and at least about 1 M to at least about 2 M salt for washing conditions. Generally, low stringency is at from about 25-30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C)% (Marmur and Doty, 1962). However, the $T_m$ of a duplex DNA decreases by 1° C. with every increase of 1% in the number of mismatch base pairs (Bonner and Laskey, 1974). Formamide is optional in these hybridization conditions. Accordingly, particularly preferred levels of stringency are defined as follows: low stringency is 6×SSC buffer, 0.1% w/v SDS at 25-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

In a preferred embodiment, competitive hybridization conditions comprise a temperature gradient in which the hybridization temperature is reduced over a period of time. In one particular embodiment, competitive hybridization is achieved with a slow temperature gradient over a period of about 7-10 minutes per degree drop. The ideal temporal length and the temperature of the temperature gradient may be determined empirically on a case by case basis.

Another aspect of the present invention provides a method for determining the likelihood that a test polynucleotide sequence differs from a driver polynucleotide sequence said method comprising preparing a composition comprising said test and driver polynucleotide sequences and a target polynucleotide sequence wherein under competitive hybridization conditions the driver polynucleotide sequence will more preferentially hybridize to the target polynucleotide sequence compared to said test polynucleotide sequence when said test polynucleotide sequence differs from said driver polynucleotide sequence by at least one nucleotide and wherein at least one of said test or driver polynucleotide sequences is labelled with a reporter molecule capable of providing an identifiable signal, subjecting said composition to competitive hybridization and non-competitive hybridization conditions and screening for the presence of a signal wherein the level of signal relative to a control is indicative of which polynucleotide sequence has competitively hybridized to said target sequence wherein an elevated level of driver hybridization to said target sequence is indicative that said test polynucleotide sequence differs from a said driver polynucleotide sequence.

In a preferred embodiment both test and driver polynucleotide sequences are labelled with a reporter molecule capable of providing an identifiable signal.

Any number of reporter molecules capable of providing an identifiable signal may be employed including those providing a fluorescent or other photonic signal, an enzyme capable of converting a substrate or a substrate convertible by an enzyme to provide an identifiable signal amongst many others. More particularly, suitable detectable molecules may be selected from a group including a chromogen, a catalyst, an enzyme, a mass tag, quantum dots, a fluorophore, a phycobilin conjugates (phytophores), a luminescent molecule, a chemiluminescent molecule, a lanthanide ion such as Europium ($Eu^{34}$), a radioisotope and a direct visual label. In the case of a direct visual label, use may be made of a colloidal metallic or non-metallic particle, a dye particle, an enzyme or a substrate, an organic polymer, a latex particle, a liposome or other vesicle containing a signal producing substance and the like. A large number of enzymes suitable for use as labels is disclosed in U.S. Pat. Nos. 4,366,241, 4,843,000 and 4,849,338. Fluorescent dye conjugated nucleotide triphosphates or phosphoramidites provide a convenient way of labelling polynucleotides during amplification for example, dCTP-Cy3, dCTP-Cy5 and dUTP-FluorX are well known reagents. Directly reactive dyes such as the psoralens are also contemplated herein. Suitable enzyme labels useful in the present invention include alkaline phosphate, horseradish peroxidase, luciferase, β-galactosidase, glucose oxidase, lysozyme, malate dehydrogenase and the like. The enzyme label may be used alone or in combination with a second enzyme which is in solution. Alternatively, a flurophore which may be used as a suitable label in accordance with the present invention includes, but is not limited to, fluorescein, rhodamine, Texas red, lucifer yellow or R-phycoerythrin and their derivatives and substitutes/analogues.

In one embodiment, the signal is also conveniently quantifiable.

Yet another aspect of the present invention provides a method for determining the likelihood that a test polynucleotide sequence differs from a driver polynucleotide sequence said method comprising preparing a composition comprising said test and driver polynucleotide sequences and a target polynucleotide sequence wherein under competitive hybridization conditions the driver polynucleotide sequence will more preferentially hybridize to the target polynucleotide sequence compared to said test polynucleotide sequence when said test polynucleotide sequence differs from said driver polynucleotide sequence by at least one nucleotide and wherein at least one of said test or driver polynucleotide sequence is labelled with a reporter molecule capable of providing an identifiable signal, subjecting said composition to competitive hybridization conditions and screening for the presence of a signal wherein the level of signal relative to a control is indicative of which polynucleotide sequence has competitively hybridized to said target sequence wherein an elevated ratio of driver polynucleotide hybridization to said target sequence is indicative that said test polynucleotide sequence differs from a said driver polynucleotide sequence said ratio being determined by the following formula $$(D:T)_{comp}/(D:T)_{non\text{-}comp}$$

wherein
D is the driver-label;
T is the test-label;
Comp is the D:T ratio under competitive hybridization conditions; and
Non-comp is the D:T ratio under control conditions.

Accordingly, yet another aspect of the present invention provides a method for determining the likelihood that a test polynucleotide sequence differs from a driver polynucleotide sequence said method comprising preparing a composition comprising said test and driver polynucleotide sequences and a target polynucleotide sequence wherein under slow hybridization conditions the driver polynucleotide sequence will more preferentially hybridize to the target polynucleotide sequence compared to said test polynucleotide sequence when said test polynucleotide sequence differs from said driver polynucleotide sequence by at least one nucleotide and wherein at least one of said test or driver polynucleotide sequence is labelled with a reporter molecule capable of providing an identifiable signal, subjecting said composition to competitive hybridization and non-competitive hybridization conditions and screening for the presence of a signal wherein the level of signal relative to a control is indicative of which polynucleotide sequence has competitively hybridized to said target sequence wherein an elevated ratio of driver polynucleotide hybridization to said target sequence is indicative that said test polynucleotide sequence differs from a said driver polynucleotide sequence said ratio being determined by the following formula:

$$(D{:}T)_{comp}/(D{:}T)_{non\text{-}comp}$$

wherein

D is the driver-label;

T is the test-label;

Comp is the D:T ratio under competitive hybridization conditions; and

Non-comp is the D:T ratio under non-competitive hybridization conditions.

In a particularly preferred embodiment, the ratio as hereinbefore described will be at least greater than 1 when the test poynucleotide sequence differs from the driver polynucleotide by one or more bases.

Even yet another aspect of the present invention provides a method for determining the likelihood that a test polynucleotide sequence differs from a driver polynucleotide sequence said method comprising preparing a composition comprising said test and driver polynucleotide sequences and a target polynucleotide sequence wherein the target polynucleotide is immobilized and wherein under competitive hybridization conditions the driver polynucleotide sequence will more preferentially hybridize to the target polynucleotide sequence compared to said test polynucleotide sequence when said test polynucleotide sequence differs from said driver polynucleotide sequence by at least one nucleotide and wherein at least one of said test or driver polynucleotide sequence is labelled with a reporter molecule capable of providing an identifiable signal, subjecting said composition to competitive hybridization conditions and screening for the presence of a signal wherein the level of signal relative to a control is indicative of which polynucleotide sequence has competitively hybridized to said target sequence wherein an elevated level of driver polynucleotide hybridization to said target sequence is indicative that said test polynucleotide sequence differs from a said driver polynucleotide sequence.

Even yet another aspect of the present invention provides a method for determining the likelihood that a test polynucleotide sequence differs from a driver polynucleotide sequence said method comprising preparing a composition comprising said test and driver polynucleotide sequences and a target polynucleotide sequence wherein the target polynucleotide is immobilized and wherein under competitive hybridization conditions the driver polynucleotide sequence will more preferentially hybridize to the target polynucleotide sequence compared to said test polynucleotide sequence when said test polynucleotide sequence differs from said driver polynucleotide sequence by at least one nucleotide and wherein at least one of said test or driver polynucleotide sequence is labelled with a reporter molecule capable of providing an identifiable signal, subjecting said composition to competitive hybridization conditions, subjecting the immobilized polynucleotide sequences to a washing step to remove unhybridized polynucleotide and screening for the presence of a signal wherein the level of signal relative to a control is indicative of which polynucleotide sequence has competitively hybridized to said target sequence wherein an elevated level of driver polynucleotide hybridization to said target sequence is indicative that said test polynucleotide sequence differs from a said driver polynucleotide sequence.

The present method may also be used to enrich for polymorphic or mutant polynucleotides.

Immobilization is preferably to a solid support which may be, for example, glass or a polymer, such as but not limited to cellulose, ceramic material, nitrocellulose, polyacrylamide, nylon, polystyrene and its derivatives, cellulose and its derivatives, polyvinylidene difluoride (PVDF), methacrylate and its derivatives, polyvinyl chloride or polypropylene. A solid support may also be a hybrid such as a nitrocellulose film supported on a glass or polymer matrix. Reference to a "hybrid" includes reference to a layered arrangement of two or more glass or polymer surfaces listed above. The solid support may be in the form of a membrane or tubes, beads, discs or microplates, or any other surface suitable for conducting an assay. Binding processes to immobilize the molecules are well-know in the art and generally consist of covalently binding (e.g. cross linking) or physically adsorbing the molecules to the solid substrate. One particular example is covalent binding to a solid phase via amide bond formation by carbodiinide mediated conjugation of aminated oligos with carboxyl or aldehyde coated solid phase moieties. If the target nucleic acid is double stranded, only one strand will be immobilized.

This embodiment of the invention is particularly suited to analysis by flow cytometry.

Accordingly, still yet another aspect of the present invention provides a method for determining the likelihood that a test polynucleotide sequence differs from a driver polynucleotide sequence said method comprising preparing a composition comprising said test and driver polynucleotide sequences and a target polynucleotide sequence wherein the target polynucleotide is immobilized and wherein under competitive hybridization conditions the driver polynucleotide sequence will more preferentially hybridize to the target polynucleotide sequence compared to said test polynucleotide sequence when said test polynucleotide sequence differs from said driver polynucleotide sequence by at least one nucleotide and wherein at least one of said test or driver polynucleotide sequence is labelled with a fluorescent reporter molecule, subjecting said composition to competitive hybridization conditions and screening for the presence of a signal by flow cytometry and/or other equivalent procedure wherein the level of signal relative to a control is indicative of which polynucleotide sequence has competitively hybridized to said target sequence wherein an elevated level of driver polynucleotide hybridization to said target sequence is indicative that said test polynucleotide sequence differs from a said driver polynucleotide sequence.

Even yet still another aspect of the present invention provides a method for determining the likelihood that a test polynucleotide sequence differs from a driver polynucleotide sequence said method comprising preparing a composition comprising said test and driver polynucleotide sequences and a target polynucleotide sequence wherein the target polynucleotide is immobilized and wherein under competitive hybridization conditions the driver polynucleotide sequence will more preferentially hybridize to the target polynucleotide sequence compared to said test polynucleotide sequence when said test polynucleotide sequence differs from said driver polynucleotide sequence by at least one nucleotide and wherein at least one of said test or driver polynucleotide sequence is labelled with a fluorescent reporter molecule, subjecting said composition to competitive hybridization conditions and, subjecting the immobilized polynucleotide sequences to a washing step to remove unhybridized polynucleotide screening for the presence of a signal by flow cytometry and/or other equivalent procedure wherein the level of signal relative to a control is indicative of which polynucleotide sequence has competitively hybridized to said target sequence wherein an elevated level of driver polynucleotide hybridization to said target sequence is indicative that said test polynucleotide sequence differs from a said driver polynucleotide sequence, said ratio being determined by the following formula:

$$(D:T)_{output}/(D:T)_{input}$$

wherein

D is the driver-label;

T is the test-label;

Output is the fluorescence D:T ratio after washing; and

Input is the fluorescence D:T ratio prior to washing.

Even still yet another aspect of the present invention provides a method for enriching a polymorphic or mutant test polynucleotide sequence in a composition comprising a test and driver polynucleotide sequence and a target polynucleotide sequence wherein the target polynucleotide is immobilized and wherein under competitive hybridization conditions the driver polynucleotide sequence will more preferentially hybridize to the target polynucleotide sequence compared to said test polynucleotide sequence when said test polynucleotide sequence differs from said driver polynucleotide sequence by at least one nucleotide and subjecting said composition to several rounds of competitive hybridization, to enrich the composition for said polymorphic or mutant test polynucleotide, if present.

The method of the present invention can at least be partly implemented using a suitably programmed computer. In particular, the preferred data processing means comprises a suitably programmed computer and the steps of the method are preferably performed using the suitably programmed computer. In various forms of the invention, the input information may take the form of values, identifiers or other data in respect of the identity. The input data may be digitized. Alternatively, for implementation of the invention, a dedicated Fast Fourier transform chip can be employed as at least part of the processing means.

Reference herein to "data processing means" includes any electronic hardware device, in combination with one or more software applications, which participates in or otherwise facilitates the analysis, calculation, computation or reconfiguration of information. The hardware device generally comprises an assemblage of electronic components and includes a computer system.

Yet still further another aspect of the present invention provides a computer program capable of controlling a method for determining the likelihood of a method for determining the likelihood that a test polynucleotide sequence differs from a driver polynucleotide sequence said method comprising preparing a composition comprising said test and driver polynucleotide sequences and a target polynucleotide sequence wherein under competitive hybridization conditions the driver polynucleotide sequence will more preferentially hybridize to the target polynucleotide sequence compared to said test polynucleotide sequence when said test polynucleotide sequence differs from said driver polynucleotide sequence by at least one nucleotide and wherein at least one of said test or driver polynucleotide sequence is labelled with a reporter molecule capable of providing an identifiable signal, subjecting said composition to competitive hybridization conditions and screening for the presence of a signal wherein the level of signal relative to a control is indicative of which polynucleotide sequence has competitively hybridized to said target sequence wherein an elevated level of driver polynucleotide hybridization to said target sequence is indicative that said test polynucleotide sequence differs from said driver polynucleotide sequence.

Another related aspect of the present invention provides an apparatus capable of determining the likelihood of a method for determining the likelihood that a test polynucleotide sequence differs from a driver polynucleotide sequence said method comprising preparing a composition comprising said test and driver polynucleotide sequences and a target polynucleotide sequence wherein under competitive hybridization conditions the driver polynucleotide sequence will more preferentially hybridize to the target polynucleotide sequence compared to said test polynucleotide sequence when said test polynucleotide sequence differs from said driver polynucleotide sequence by at least one nucleotide and wherein at least one of said test or driver polynucleotide sequence is labelled with a reporter molecule capable of providing an identifiable signal, subjecting said composition to competitive hybridization conditions and screening for the presence of a signal wherein the level of signal relative to a control is indicative of which polynucleotide sequence has competitively hybridized to said target sequence wherein an elevated level of driver polynucleotide hybridization to said target sequence is indicative that said test polynucleotide sequence differs from said driver polynucleotide sequence.

Another aspect contemplates a use of flow cytometry for a method for determining the likelihood that a test polynucleotide sequence differs from a driver polynucleotide sequence said method comprising preparing a composition comprising said test and driver polynucleotide sequences and a target polynucleotide sequence wherein under competitive hybridization conditions the driver polynucleotide sequence will more preferentially hybridize to the target polynucleotide sequence compared to said test polynucleotide sequence when said test polynucleotide sequence differs from said driver polynucleotide sequence by at least one nucleotide and wherein at least one of said test or driver polynucleotide sequence is labelled with a reporter molecule capable of providing an identifiable signal, subjecting said composition to competitive hybridization and non-competitive hybridization conditions and screening for the presence of a signal wherein the level of signal relative to a control is indicative of which polynucleotide sequence has competitively hybridized to said target sequence wherein an elevated ratio of driver polynucleotide hybridization to said target sequence is indicative that said test polynucleotide sequence differs from said driver polynucleotide sequence, said ratio being determined by the following formula:

$$(D:T)_{comp}/(D:T)_{non-comp}$$

wherein

D is the driver-label;

T is the test-label;

Comp is the D:T ratio under competitive hybridization conditions; and

Non-comp is the D:T ratio under non-competitive hybridization conditions.

The present invention is further described by further non-limiting Examples.

Example 1

Oligonucleotides

All oligonucleotides (75 base pairs) were purchased from Gibco-BRL/Life Technologies. The sequence used corresponds to bases 82 to 8 nucleotides upstream of the transcription start site of the human B-globin gene (Casey, J., 1977) (FIG. 1). Wild type alleles and 7 corresponding alleles differing by one base were produced as well as the exact complement (MTARGETN) to the wild type sequence. The 7 mutant alleles were synthesized with FAM phosphoramidite at the 5' end. One wild type sequence prep, MDRIVERH, was labelled with HEX. MDRIVER was also produced with Cy5 added to the 5' end.

Example 2

Post-Synthesis Labelling of Amine Terminated Oligo Nucleotides

Oligonucleotide (4 nM) were EtOH precipitated 2× with NaOAc and 95% EtOH and then resuspended in $H_2O$ at 400 µm final concentration. 40 µl 0.15M $NaCHO_3$ buffer, pH 8.3, was added along with 1 µM of the appropriate NHS ester resuspended in DMSO at a final concentration of 1.0M. The reaction solution was mixed gently every few minutes for 1 hour and then allowed to incubate overnight in the dark at RT. Labelling reactions were then made 0.3M for NaOAC and precipitated with 3 volumes of 95% EtOH. Pellets were resuspended in 2.5 ml $H_2O$ and run over PD-10 desalting columns (Amersham-Pharmacia) and eluted in 3.5 ml $H_2O$. Eluates were concentrated in a vacuum centrifuge to 40 µM final concentration.

Example 3

Conjugation of MTARGETN to COOH Magnetic Beads

Paramagnetic beads (2.5 XM-200 Advanced Biotechnologies) were washed 8 times in 500 µL diethylpyrocarbonate treated $H_2O$. These beads were conjugated to 2 µM of MTARGETN in 2 ml 0.1 M 1-methylimidazole (pH 6.9) made 5 mM for 1-Ethyl-3-(3-Dimethylaminopropyl) carbodiimide Hydrochloride (EDC, Pierce). The mixture was rocked for 40 hours at room temperature. At the end of the incubation, the beads were washed 4 times with 750 µL of WB (50 mM NaCl, 10 mM tris, pH 8.5). Beads were stored in 5 ml of 15% PEG, 5 mM EDTA.

Example 4

Hybridization Conditions

Hybridizations were performed with the target:driver:test ratio of 1:2:10 (1.25:2.5:25 pMoles). Reactions were performed in 15% PEG, 10 mM Tris and either 10 or 20 mM NaCl in 30 µL total volume. Each reaction was split into two equal 15 µl aliquots for fast or slow hybrization. For fast hybridizations, the aliquot was denatured 5 minutes at 82° C. and then fast ramped at 42° C. and held for 30 minutes. For slow hybridizations, after an initial denturation at 82° C., the temperature was fast ramped to 72° C. and then temperature was reduced 1 C every 10 minutes until 42° C. This represented denaturation at Tm+20° C., slow temperature gradient from Tm+10° C.→Tm−20° C. (72° C.→42° C.). Post hybridization washes included 5×500 µl washes with WB for the gel based experiments, and no washes for the flow. The target: driver:test ratio may be varied to optimise results.

Example 5

Acrylamide Gel Electrophoresis

Washed beads were resuspended in 8 µl LB (84% Formamide, 16% mG/ml blue dextran) and incubated 5 minutes at 85° C. to elute the captured strands. DNA was electrophoresed on a 6% acrylamide, 6.25 urea gel using an ABI 377 automated sequencer (PE systems) at 3000 v for 2 hours. Peak areas were calculated using ABI software Genescan v. 3.1 (PE Biosystems).

Example 6

Competitive Hybridization

DNA:DNA hybridization reactions are dependent upon concentration of nucleic acids, temperature and ionic strength of the solution. Theoretical optimal annealing temperatures can be calculated from empirically derived formulae (Casey, J., 1977) and are related to the Tm, the temperature at which homoduplexes and single stranded DNA are at equilibrium (Bonner, T. I., 1973). Generally, the Tm of a solution less 20-25° C. is the optimal binding temperature. We chose 75-mers whose theoretical Tm at 10 mM was 62° C. and we performed fast and slow annealing hybridization experiments in which mutant or wild type FAM labelled test DNA was present in 5 fold excess over wild type HEX DNA. Each reaction contained an equal and limiting amount of immobilized target DNA. In the experimental design, the fast reaction should not favour either DNA species' hybridization to target. On the other hand, the slow hybridization was a competitive hybridization, presumably due to the rapid annealing of wild type DNA to target at a temperature slightly higher than the Tm of the corresponding mutant:target reaction (FIG. 2). We found that this temperature gradient was more than adequate for the discrimination of sequences containing either wild type or a mixture of wild type and mutant sequences.

Example 7

Gel-Based Assays

For this experimental approach to succeed, a method must be chosen in which DNA from driver and test sequences can be differentiated. Our protocol used HEX labelled (gel based tests) or Cy5 labelled (for flow cytometer based tests) wild type DNA and FAM labelled test DNA. After competitive and non-competitive annealing, amounts of binding of each type of DNA to immobilized target was determined by use of ABI 377 automated sequencer (FIG. 3) and Genotyper v. 2.1 (ABI) to determine peak areas for each color (gels tracked and evaluated in single blind manner). The wild type:mutant (HEX:FAM) ratios were then calculated for both the fast and slow conditions (FIG. 5, H:F columns) with a compensation value of 4.0. This value was chosen because the expected Fast hybridization excess of FAM label to HEX was 5.0. The mean excess from the experiment was approximately 20.0, a factor 4 greater due to the spectral characteristics of the dyes involved. The mutation detection index (MDI) was calculated as the ratio of the H:F$^{(S)}$/H:F$^{(F)}$. An MDI score of more than 4 would be expected to be strong evidence of a mutation, judging from results from previous investigators (Terouanne, B. et al., 1992; Oka, T. et al., 1994). All of the slow annealing reactions in which mutant DNA was mixed with wild type showed an even stronger homoduplex bias (FIG. 5) with MDI scores well over 100. It was difficult to accurately ascertain many of the FAM binding results in the mutant reactions because no test color (FAM) was detectable at the background level of the system (FIG. 5, FIG. 3). In these cases, the level was set to the system's background cut off value of 15 to avoid division by 0.0 in the ratio calculation.

We were surprised that positional effects of the mutations were apparently non-existent even in long oligonucleotides of at least 500. Mutations centrally located (M-49T, M-37T) and those less than 10 bases from either end of the DNA (M-79A, M-17G) did not show significant differences in MDI scores. Also, the NaCl concentrations had no effect on the results. It must be noted, though, that high concentrations of PEG may have modified any possible differences in ionic strength.

Example 8

Flow-Cytometry Assays

Flow cytometry was performed on a Facscalibur flow cytometer (Becton-Dickinson).

The flow experiments duplicated the results of the gel based assay (FIG. 4). In these experiments, MTARGET DNA was biotinylated at the 5' end and conjugated to 10.9 uM superavidin coated beads (Bang's Labs, Indiana) at a ratio of $1.7 \times 10^7$ molecules per bead. Cy5 labelled wild type Driver DNA was added in 2× excess and the test DNAs were in 10× excess. For each reaction, approximately 200,000 beads were used and data was obtained for 4,000 to 10,000. All seven mutations tested showed pronounced positive shifts in wild type Driver binding in the competitive hybridization condition. A slight difference in the peak shifts were obtained in the two mutants which were less than 10 bases from the ends. This is not an unexpected result and the detection of the mismatch for these as well as the more centrally located mutations was unambiguous.

We have shown that mismatches can be detected in non-gel electrophoresis format. This particular approach is especially noteworthy because it combines a general hybridization scheme with the speed and power of flow cytometry. The next phase of this development is to multiplex many experiments into one flow experiment.

This approach will be useful for the design of various types of genetic analyses. The obvious use will be in the quick and accurate genotyping of individuals at specific loci. Since this is a mutation scanning approach as opposed to an allele specific test, new mutations will be easily spotted and characterised by DNA sequencing. The incorporation of additional controls to match common polymorphisms would assist this process of identifying those amplicons with rare mutations. Also, these additional controls would be useful for confirmation of homozygous versus heterozygous state in test individuals.

Besides single point mutations, microsatellite markers can be efficiently scored in genomic mapping experiments using this technique. Presently, these markers depend upon sizing by gel electrophoresis, but discrimination of dinucleotide repeats in typical sized amplicons (150-400 bp) should be easily accomplished in this gel-free method.

Beyond the genetic analysis of known disease genes, this technique will be valuable in the identification of single nucleotide polymorphisms (SNPs). SNPs will be the genetic tool for mapping in the next few years, but the ability to find them for specific crosses of laboratory stocks or for human populations with different allelic frequencies than standard will be problematic. The SIFT will be quite useful not only in the identification of these new SNPs, but also in their application in mapping experiments.

Example 9

Strand Specific Binding Systems

The SIFT system uses:
(i) a Target strand of known sequence optionally bound to a solid phase;
(ii) a wild type competitor (driver) strand which is the exact complement of the Target strand;
(iii) a test strand which can be differentiated from the wild type competitor and which is complementary to the Target; and
(iv) a method of assessing the relative amounts of wild type competitor and test To further evaluate the technique several components of the test system have been assessed.

The optimization experiments described below used biotin-streptavidin systems. Covalent bonding to a solid phase via amide bond formation such as by carbodiimide mediated conjugation of aminated oligos with carboxyl or aldehyde coated solid phase is also contemplated.

While the major thrust of this work has been the development of a gel free system for mutation scanning, optimization experiments are conveniently done using gel electrophoresis.

Immobilization to beads is specially preferred.

First, several beads from several different suppliers were tested and evaluated for both yield, specificity of binding, ease of handling, and cost. Further optimization experiments described below were performed with magnetic particles (Scigen)

Each of the following tests were performed with 2 mutant 75-mers, 17G and 67A, wild type (wild type), and the "heterozygotes" of these strands made by mixing equimolar amounts of the mutants with the wild type. The wild type competitor in these experiments was made with a 36 Carbon spacer between the 5' end of the oligonucleotide and the HEX moiety. This provided a roughly 1 base size difference between the wild type strand and the test strand. This reduced the spectral overlap and made quantification easier and more reliable. This difference in both mass and fluor for differentiation of the two strands may also be detected by mass spectrometry. This set of 5 DNAs will be referred to below as "test DNAs."

Buffer Constituents

The competitive effects of this technique were assessed with test DNAs in various salts in concentrations varying from 0.1 to 2.0 Molar.

Tetra alkyl ammonium salts were found to enhance the competitive effects profoundly in concentrations between 0.2 and 1.0 M. Tetra Methyl Ammonium Chloride (TMAC) and Tetra Ethyl Ammonium Chloride (TEAC) in concentrations of 0.2M to 1.0M were found to enhance the homoduplex binding 10 fold over the 10 mM NaCl original condition. NaCl concentrations up to 2.0 M had no such affect when present as the only salt. On the other hand, when NaCl was present in 1.0 M concentration with 0.5 or 1.0 M TMAC, the effects were equivalent to those observed with TMAC alone. The addition of the NaCl to the reaction aided the binding to the streptavidin coated particles.

0.5M TMAC was the condition used for the optimization and robustness experiments described below. For many of these tests, duplicates were made with 1.0 M NaCl and no differences were observed between the paired samples.

Reaction Volumes

It was hypothesised that reduced volume would enhance the competition. Reaction volumes of 5, 10 and 20 microliters were tested. Each reaction contained approximately 4 picomoles of test DNA. No differences were observed. Previous work used both 50 and 100 uL volumes with success. These data support the robustness of this technique for both large and small reaction volumes.

Wash Conditions

SIFT depends upon the separation of the hybridization products to the specific target from all unbound strands. Thus, the washing conditions are critical. It was hypothesized that NaCl and detergent would be necessary constituents of the washes; NaCl for maintaining the integrity of the duplex on the solid phase, and detergent for the maintenance of the monodispersed consistency of the particles. Surprisingly, both 0.01 M tris, pH 8.1 and water were found to be equivalent to buffers containing either SDS or Tween 20 detergents. The particles were not significantly more clumped nor more difficult to handle when washing in detergent free solutions.

Na concentrations were also not problematic. It was thought that low salt concentrations would give false results of the competitive hybridization. SSC concentrations of 0.1×, 0.2×, 1×, and 2× gave virtually identical results to either water or tris washes. On the other hand, SSC concentrations greater than 2× increased non-specific binding.

The number of washes needed for SIFT was determined. In both water and tris, 2×100 uL washes were sufficient to remove all detectable non-specific binding. For salt washes, 3 washes were sufficient. The standard procedure for the remaining optimization experiments were 2 0.01M tris, pH 8.1 washes of 100 uL.

Ratio Testing

Several ratios of Target:Wild type competitor: test were evaluated. All ratios had at least a 5 fold excess of competitor and test to target. For the scanning type experiments, only ratios in which test excess was present were assessed. Theoretically, the best ratio for detection of heterozygotes would be 1 wild type competitor:1 test strand. This was confirmed experimentally and is summarized in the FIG. 6.

Temperature Gradient Depth and Length

For this technique to be useful as a high throughput method, it is important that the reaction time is slow enough for the competition, but fast enough that the temperature controlling instrument used for the gradient can be used several times a day. In the experiments described above, the standard condition used was a gradient from 90° C. to 50° C. with a 10 minute per degree drop. This was thus a 400 minute procedure. For incorporation of SIFT in genomic scale genetics programs this time is reduced by either reducing the length of the gradient and/or the time of the gradient.

The first set of depth experiments (FIG. 7) found the upper limit of the gradient for efficient detection of competitive effects. Starting with 99° C., several temperatures were designated as the upper limit of the slow temperature decline. Each gradient tested in this set of experiments ended at 50° C. and length of the gradient was set at 10 minute per degree drop. In the table below, the numbers on the lower level reflect the starting point of the gradient after an initial 2 minute melt at 99° C. This represents the results from one homozygote, 17G.

The effect was completely absent below the threshold and full above the threshold. This cutoff was approximately 20° C. higher than the theoretical Tm of 65° C.

The converse experiment was performed to find the lower limit of the gradient. Here, the same reaction conditions were used, with the gradient starting at 90° C. The end points consisted of several endpoints below the upper limit determined in the experiment above. As above, the data represents typical results from 1 homozygote, 17G (FIG. 8).

This result was not unexpected given the upper limit result. These data suggest that the gradient depth need be only 15-20° C. These data were generated using 75 mers. If longer oligos or PCR products were to be used, the gradient depth would be even shorter due to the higher Tm of the longer DNA.

Similar experiments were carried out using a 90-75° C. gradient of different lengths. The lengths tested ranged from immediate (99° C. for 2 minutes→fast ramp to 50° C.) to the control length of 10 minutes per degree drop. FIG. 9 shows the data for the 17G homozygote. These data show that a mutation scanning experiment for a 75-mer (or greater) could be reliably tested for genetic heterogeneity in a time of less than 2 hours.

Example 10

Multiplexing and Different Gel Free Platforms

The method may be multiplexed in several different platforms. For example, different sized microspheres with different fluorescent tags may be employed. Such a system would allow several dozen or more separate DNA scans per reaction. The results would then be quantified by flow cytometry. This would obviate the need for magnetic separation and clean-up.

Alternatively, a complex reaction of several independent hybridizations could be bulk purified by biotin-streptavidin purification, and then stripped and used to probe an array of the target DNAs.

A third platform is the use of mass tagging the competitor (driver) and test strands and resolving ratios by mass spectrometry. This would require the employment of not only a mass tag but a cleavable site within the primer carrying the tag. Several systems exist including light cleavable phosphoramidites and Uracil cleavage with Uracil N-glycosylase.

Example 11

Single Nucleotide Polymorphism Detection

An increasingly popular subset of mutation detection is SNP detection. SIFT could be used in a variety of formats. For example, biotin may be used to label the primer for generation of test PCR product. This is then subjected to competitive hybridization with differently labelled oligos representing the sequence of both alleles. Results of the hybridization are determined by binding to streptavidin, stripping and probing an array.

The competitive binding can be done before or after binding of the DNA to the solid phase. In these examples, 35-mers are used as the reporting competitive probes. Their Tm in the conditions used here are about 85° C. and so can be used in standard streptavidin-biotin experiments since the critical temperature of 90° C. does not have to be reached. This temperature is where the streptavidin will lose integrity and binding to biotin will be lessened. Also, for many polystyrene microspheres, 90° C. marks the threshold of tolerance of the sphere.

Another approach is to array PCR test products and then perform the competitive hybridization on glass.

Mutation Detection Enhancement by Multiple Rounds of Competitive Hybridization

These above data show a competitive advantage of at least 5 fold. In other words, after one round of SIFT, homoduplexes will form at a rate at least 5 times that of heteroduplexes. In the descriptions of the applications above, the ratio was determined by determining the different amounts of each captured strand bound to a limiting amount of target strand. In this application, heterozygous DNA is first used in a SIFT type subtraction round. Instead of collecting and assaying the target:capture complex, the supernatant is instead repeatedly subjected to competitive hybridization. Given an 80% competitive advantage of the wild type allele over the mutant allele, a 5 fold excess of the test DNAs over immobilizable target Wild type DNA, and equal amounts of wild type and mutant alleles, an approximately 4 fold enrichment of mutant sequences should be present in the supernatant after 3 rounds of subtraction. This would make this technique usable for mutation scanning for not only germline mutations but somatic mutations as well.

Mutation Detection Enhancement by Synthetic Mismatch

Since it is possible to gain a 5 fold advantage for exact matches over single point mismatches, it follows that multi-point mismatches should be out competed by single mismatches. This may be a way of enhancing the competitive effects by essentially ablating any residual mismatch binding, but at the expense of needing more starting material. These experiments used amounts of DNA in line with present PCR capabilities.

Example 12

Polymorphism Enrichment

In this experiment, mutant (test) to wild type (driver) ratios of 0:1, 1:1, 4:1, 10:1, and 1:0 were tested. In this application, instead of using a wild type competitor, the FAM labeled ratios were first subjected to competitive hybridization (99-80 degrees; 8 minutes per degree drop) to a relatively high amount of target DNA. In this experiment, a 10 fold excess of total test DNA to Target was employed. The resulting duplexes were removed by magnetic separation of the solid phase. The unbound supernatants, enriched by the competitive hybridization for mutant sequence, were subjected to a second and a third round of competition. After each round, 10% of the reaction was saved for a "readout" competition in which a wild type competitor labelled with HEX was added and this mixture was subjected to the same competition. The results are shown in FIG. 10. In effect, even a 10:1 ratio of wild type:mutant could be detected with this enrichment strategy. Even though the relative difference was not large, it was clearly larger than controls. The different ratios were quite clearly called. One use for this type of protocol would be for the detection of rare alleles such as mutant alleles in tumor tissue.

Example 13

SIFT Using PCR as Both Target and Test

In this application, DNAs differing by a single base were obtained by PCR. The template DNAs were two mouse strains, BL/6 and SJL. The primers used were:

(BL/6 specific forward):
(Seq. ID No. 10)
FAM--GCTAAAAACTGGGACTTTGTG (SJL specific forward):
(Seq. ID No. 11)
HEX--GGCTCAAGCTAAAAACTGGGACTTTGTG (Reverse):
(Seq. ID No. 12)
    AGTATCCACCCCCAGAGCTTG (Reverse-biotin):
(Seq. ID No. 12)
BIO--AGTATCCACCCCCAGAGCTTG First, BL/6 target/wild type competitor DNA was made by PCR of BL/6 with BL/6 specific forward primer and biotin reverse primer. SJL and BL/6 test DNAs were made by amplification of appropriate DNAs with a FAM labeled strain specific forward primer and unlabeled reverse primer. A "heterozygote" sample (SJL:BL/6) was constructed by combining equal portions of these two test samples. DNAs were mixed in 10:1 ratio of Test:target and subjected to SIFT gradient of 99-80 for 10 minutes per degree drop. Non-competitive data and competitive data were compared after gel electrophoresis and quantitation using Genescan software. The non-competitive data were derived as follows. After competitive hybridization a portion of this mixture (say 10%) was used as the control prior to any selection of bound species. This was then the input fluorescent ratio having been subjected to the same conditions as the competitive hybridization, but having no selection of duplexes bound to immobilized target. The results are shown in FIG. 11. The 4 fold competitive advantage in the homozygote and the 1.8 fold in the Heterozygote is especially important given that this is a mismatch at the extreme edge of the amplicon, the very first base added 3' of the forward primer.

Example 14

Different Platforms for the Present Method

SIFT has a wide range of applications for example, gel electrophoresis, flowcytometry and mass spectroscopy. SIFT also works on several different platforms such as:
  (i) Screening tool for known polymorphisms in known disease genes such as hypertrophic cardiomyopathy, colon and breast cancer, and cystic fibrosis.
  (ii) Determination of tissue typing: the MHC locus is very polymorphic and determines the tissue type of an individual. In humans, the HLA region is quite well characterized and this technique could be quite useful in very rapid genotyping in this area
  (iii) Full genome scanning: It will be possible to quickly convert sequence length polymorphisms to SIFT genotyping. See Example 15.
  (iv) Specific locus testing: It will be possible to scan many genes for unknown novel mutations.
  (v) SNP: Many approaches to SNPs have been developed. Virtually all require PCR followed by a second enzymatic step requiring clean-ups and additional reagents such as labeled ddNTPs, polymerase, and sequence specific oligonucleotides. SIFT can be used in a single step using instrumentation already available. An outline of some of the approaches is shown in FIG. 12) and Example 13.
  (vi) Scanning for somatic mutations: This method is sensitive enough in one round to detect heterozygosity in germ line. It is also theoretically sensitive enough to scan for unknown rare somatic mutations in non-germ line tissue such as tumour tissue or lymphocytes. See Example 12.

(vii) SIFT as scanning tool for epigenetic factors of gene expression. SIFT could also be used as a tool for scanning methylation patterns in DNA. In this application, bisulfite treated DNA could be sequenced and then compared to non bisulfite treated products as targets. This application could be expanded to test for other DNA adducts.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

Example 15

Use of SIFT in SLP Detection System

Small tandem repeats are very common in metazoan genomes and have been exploited as genetic markers in several organisms. A typical mapping protocol consists of several steps, namely, 1) DNA isolation, 2) PCR from many dozens or hundreds of loci, 3) electrophoresis of individual PCR reaction products, and 4) scoring of gels. The running and scoring of PCR products is expensive and slow. Full automation of these two steps is possible with a SIFT approach.

In the following example, mouse gDNA from BL/6 and SJL were compared. A region was found differing by an insertion in BL/6 of approximately 50 bases. Primers were designed around the insertion/deletion and manufactured such that the forward primer was either unlabeled or biotinylated, and reverse primers were labeled with either BODIPY-Fl (a Fluroescein substitute), or BODIPY-TMR (Tetramethylrhodamine substitute). PCR products were produced to yield products with following configurations:

| DNA | Forward Primer | Reverse Primer |
| --- | --- | --- |
| BL/6 | bio | BODIPY-Fl |
| BL/6 | — | BODIPY-TMR |
| SJL | bio | BODIPY-Fl |
| SJL | — | BODIPY-TMR |

In this design, bio/Fl DNA was used as both target and driver, while –/TMR DNA was the test.

DNA was added in approximately 5 fold test excess with BL/6 as target.

BIBLIOGRAPHY

Bonner and Laskey, *Eur. J. Biochem* 46: 83, 1974.
Bonner, T. I., (1973) *J. Mol. Biol.* 81: 123-135.
Casey, J. and Davidson, N. (1977) *Nucleic Acids Res.* 4: 1539-1552.
Cotton R. G. et al. (1988) *Proc. Natl. Acad. Sci.* 85: 4397-4401.
Foode. R and Losekoot, M. (1994) *Hum. Mutat.* 3: 86-94.
Hacia, J. G. et al. (1996) *Nat. Genet.* 14: 441-447.
Holland P. M. et al. (1991) *Proc. Natl. Acad. Sci. USA* 88: 7276-7280.
Lu, A. L. and Hsu, I. C. (1992) *Genomics* 14: 249-255.
Marmur and Doty, *J. mol. Biol.* 5: 109, 1962.
Myers, R. M. et al. (1985) *Science* 230: 1242-1246.
O'Donovan M. C. et al. (1998) *Genomics* 52: 4449.
Oka, T. et al (1994) *Nucleic Acids Res.* 22: 1541-1547.
Orita, et al. (1989) *Proc. Natl. Acad. Sci.* 86: 2766-2770.
Parsons, B. L. and Heflich, R. H. (1997) *Mutat. Res.* 374: 277-285.
Ririe, K. M. et al. (1997) *Anal. Biochem.* 245: 154-160.
Roest, P. A. et al. (1993) *Hum. Mol. Genet.* 2: 1719-1721.
Schwartz, H. et al. (1998) *Hum. Mol. Genet.* 7: 1029-1032.
Sosnowski, R. G. et al. (1997) *Proc. Natl. Acad. Sci. USA:* 1119-1123.
Terouanne, B. et al. (1992) *Anal. Biochem.* 205: 193-199.
Youil, R et al. (1995) *Proc. Natl. Acad. Sci. USA* 92: 87-91.

The invention claimed is:

1. A method of determining a single nucleotide mutation or a single nucleotide difference between a test polynucleotide, from a first nucleic acid sample from a first subject, and a driver polynucleotide sequence, from a second nucleic acid sample from a second subject, the method comprising:
   (a) producing the test polynucleotide which corresponds to the driver polynucleotide by amplification from the first nucleic acid sample with a pair of forward and reverse primers including a first label whereby the test polynucleotide is labeled with a first reporter molecule capable of providing a first identifiable signal;
   (b) producing complementary driver and target polynucleotides by amplification from the second nucleic acid sample with a pair of forward and reverse primers that amplify the same region in (a) and include a second label whereby the driver polynucleotide is labeled with a second reporter molecule different from the first reporter molecule and capable of providing a second identifiable signal
   (c) preparing a composition comprising the labeled test and driver polynucleotides in solution and a target polynucleotide immobilized on a solid support and unlabeled with the first or second reporter molecules wherein the ratio of labeled test to driver polynucleotides present in the composition is from 2:1 to 10:1; and
   (d) flow cytometry screening to detect immobilized first and second identifiable signals after subjecting said composition to competitive hybridization conditions comprising a temperature gradient, wherein the driver polynucleotide will more preferentially hybridize to the target polynucleotide than said test polynucleotide when said test polynucleotide differs from said driver polynucleotide by at least one nucleotide;
   (e) determining said test polynucleotide differs from said driver polynucleotide by at least one nucleotide when the (D:T)comp is greater than the (D:T)non-comp and said test polynucleotide sequence is not different from said driver polynucleotide sequence when (D:T)comp is not greater than the (D:T)non-comp,
   wherein
      D is the driver-label;
      T is the test-label;
      (D:T)comp is the D:T ratio under the competitive hybridization conditions; and
      (D:T)non-comp is the D:T ratio under the non-competitive hybridization conditions
         wherein the complete nucleotide sequence of either the test polynucleotide and/or the driver polynucleotide is unknown.

2. The method of claim 1, wherein the single base mutation is centrally-located in said test polynucleotide.

3. The method of claim 1, wherein the single base mutation is less than 10 bases from either end of the test polynucleotide.

4. The method of claim 1, wherein the non-competitive hybridization conditions is from 25° C.-42° C.

5. The method of claim 1, wherein the competitive hybridization conditions is at least 65° C.

6. The method of claim 1, wherein the temperature gradient comprises a period of about 0.2-10 minutes per degree drop.

7. The method of claim 1, wherein the temperature gradient is from about Tm+10° C. to about Tm−20 to −25° C.

8. The method of claim 1, wherein the amounts of the target, driver and test polynucleotides are provided in a ratio of 1:2:10.

9. The method of claim 1, wherein the amounts of the driver and test polynucleotides are provided in a ratio of 1:5.

10. The method of claim 1 wherein the single base mutation is in one allele.

\* \* \* \* \*